US009023364B2

(12) United States Patent
Kanda et al.

(10) Patent No.: US 9,023,364 B2
(45) Date of Patent: May 5, 2015

(54) VACCINE ANTIGEN CAPABLE OF INDUCING CROSS-REACTING AND NEUTRALIZING ANTIBODY AGAINST HIGH-RISK-TYPE HUMAN PAPILLOMAVIRUS

(75) Inventors: Tadahito Kanda, Tokyo (JP); Kazunari Kondo, Tokyo (JP)

(73) Assignee: Japan Health Sciences Foundation, Tokyo (JP)

( * ) Notice: Subject to any disclaimer, the term of this patent is extended or adjusted under 35 U.S.C. 154(b) by 597 days.

(21) Appl. No.: 12/452,305

(22) PCT Filed: Jun. 25, 2008

(86) PCT No.: PCT/JP2008/061569
§ 371 (c)(1),
(2), (4) Date: Mar. 25, 2010

(87) PCT Pub. No.: WO2009/001867
PCT Pub. Date: Dec. 31, 2008

(65) Prior Publication Data
US 2010/0183648 A1 Jul. 22, 2010

(30) Foreign Application Priority Data
Jun. 26, 2007 (JP) .................................. 2007-167154

(51) Int. Cl.
*A61K 39/12* (2006.01)
*A61K 39/00* (2006.01)
*C07K 14/005* (2006.01)
*C12N 7/00* (2006.01)

(52) U.S. Cl.
CPC ............... *A61K 39/12* (2013.01); *C07K 14/005* (2013.01); *C12N 7/00* (2013.01); *A61K 2039/5258* (2013.01); *C07K 2319/40* (2013.01); *C12N 2710/20022* (2013.01); *C12N 2710/20034* (2013.01)

(58) Field of Classification Search
CPC ........... A61K 39/12; A61K 2039/5258; C12N 2710/20011; C12N 2710/20034; C07K 2319/40; C07K 14/005
See application file for complete search history.

(56) References Cited

FOREIGN PATENT DOCUMENTS

| EP | 1410805 A1 | 4/2004 |
|---|---|---|
| JP | 2007-045746 A | 2/2007 |
| WO | WO-95/31532 A1 | 11/1995 |
| WO | 2005/097987 A1 | 10/2005 |
| WO | WO-2007/002007 A2 | 1/2007 |
| WO | WO-2007/018049 A1 | 2/2007 |

OTHER PUBLICATIONS

Kanda and Kondo, Human Vaccines, Jan. 2009, 5, 1:43-45.*
Meijia et al., J. Virol., 2006, 80(24):12393-12397.*
Pastrana et al., Virology, 321:205-216 (2004).
Villa et al., Lancet Oncol, 6:271-278 (2005).
Harper et al., Lancet, 367:1247-1255 (2006).
Kondo et al., Virology, 358:266-272 (2007).
Kondo et al., Journal of Medical Virology, 80:841-846 (2008).
The Annual Meeting of the Japanese Cancer Association, vol. 66, Aug. 25, 2007.
Kanamitsu, Kotai Kogaku Nyumon, pp. 63-67 (1994) and English language translation.
Varsani et al., Journal of Virology, 77(15):8386-8393 (2003).
Matsumoto et al., Jpn. J. Cancer Res., 88:369-375 (1997).
Kawana et al., Virology, 245:353-359 (1998).
Kawana et al., Journal of Virology, 72(12):10298-10300 (1998).
Kawana et al., Journal of Virology, 73(7):6188-6190 (1999).
Kawana et al., Vaccine, 19:1496-1502 (2001).
Kawana et al., Vaccine, 21:4256-4260 (2003).
Roden et al., Virology, 270:254-257 (2000).
Chen et al., Molecular Cell, 5:557-567 (2000).
Slupetzky et al., Journal of General Virology, 82:2799-2804 (2001).
Sadeyen et al., Virology, 309:32-40 (2003).
Embers et al., Journal of Virology, 76(19):9798-9805 (2002).
Embers et al., Vaccine, 22:670-680 (2004).
Christensen et al., Virology, 223:174-184 (1996).
Carter et al., Journal of Virology, 77(21):11625-11632 (2003).
Written Opinion issued in Singapore Patent Application No. 200908485-6 dated Jan. 1, 2011.
Search Report issued in Singapore Patent Application No. 200908485-6 dated Jan. 1, 2011.
Decision on grant of patent for Invention for Russian Patent Application No. 2009148037 with English Translation.
European Search Report for corresponding EP Patent Application No. 08777585.4, mailed Nov. 15, 2013.
Carter et al. "Identification of Human Papillomavirus Type 16 L1 Surface Loops Required for Neutralization by Human Sera," *Journal of Virology*, vol. 80, No. 10, 2006, pp. 4664-4672.
Slupetzky et al. "A papillomavirus-like particle (VLP) vaccine displaying HPV16 L2 epitopes induces cross-neutralizing antibodies to HPV11," *Vaccine*, vol. 25, No. 11, 2007, pp. 2001-2010.
Kanda "Development of an HPV Vaccine for a Broad Spectrum of High-risk Types," *Human Vaccines*, vol. 5, No. 1, 2009, pp. 43-45.
1st Official Action for CN patent application No. 200880021650.7 issued on May 29, 2012.

(Continued)

*Primary Examiner* — Stacy B Chen
(74) *Attorney, Agent, or Firm* — Mintz Levin Cohn Ferris Glovsky and Popeo, P.C.; David G. Conlin; Christopher R. Cowles

(57) ABSTRACT

Disclosed is a vaccine antigen capable of inducing a cross-reacting and neutralizing antibody directed against a high-risk-type human papillomavirus. Specifically disclosed are: a chimeric protein comprising an L2-epitope of a human papillomavirus (HPV) type-16 inserted in a loop region of a human papillomavirus type-16 L1 protein; and a capsid which is a particle formed by the chimeric protein. The loop region to which the L2-epitope is to be inserted is located between an amino acid residue at position-430 and an amino acid residue at position-433. The L2-epitope has an amino acid sequence represented by any one of the following formulae: LYKTCKQAGTCPPDIIPKVEG (SEQ ID NO: 2) (18-38 L2-epitope); GGLGIGTGSGTGGRTGYIPL (SEQ ID NO: 3) (56-75 L2-epitope); and DPVGPLDPSIVSLVEESSFI (SEQ ID NO: 4) (96-115 L2-epitope).

8 Claims, 7 Drawing Sheets

(56) References Cited

OTHER PUBLICATIONS

1st Official Action for MX patent application No. MX/a/2009/014246 issued on Mar. 8, 2012.
2nd Official Action for MX patent application No. MX/a/2009/014246 issued on Oct. 5, 2012.
3rd Official Action for MX patent application No. MX/a/2009/014246 issued on Feb. 15, 2013.
Patent Examination Report No. 3, issued Sep. 30, 2013, in corresponding Australian Patent Application No. 2008268014.
International Search Report for PCT/JP2008/061569 mailed Jul. 29, 2008.
Official Action for RU patent application No. 2009/148037 received on Mar. 30, 2012.
Decision to Grant a Patent, issued Mar. 31, 2014, in Japanese Patent Application No. 2009-520619.
Third Official Action for Chinese Patent Application No. 200880021650.7 issued Nov. 26, 2013.
Fourth Official Action for Mexican Patent Application No. MX/a/2009/014246 issued Oct. 28, 2013.
Second Official Action for JP patent Application No. 2009-520619 issued on Jan. 7, 2014.
Breitburd et al. "Immunication with viruslike particles from cottontail rabbit papillomavirus (CRPV) can protect against expermental CRPV infection." *J.Virol.* 69(6): 3959-3963, 1995.
Jansen et al. "Vaccination with yeast-expressed cottontail rabbit papillomavirus (CRPV) virus-like particles protects rabbits from CRPV-induced papilloma formation." Vaccine 13(16): 15109-1514,1995.
Christensen et al "Immunization with viruslike particles induces long-term protection of rabbits against challenge with cottontail rabbit papillomavirus." J. Virology. 70(2): 960-965, 1996.
Kirnbauer et al. "Virus-like Particles of Bovine Papillomavirus Type 4 in Prophylactic and Therapeutic Immunization" Virology 219, 37-44, 1996.
Christensen et al. "Assembled baculovirus-expressed human papillomavirus type 11 L1 capsid protein virus-like particles are recognized by neutralizing monoclonal antibodies and induce high titres of neutralizing antibodies." *J Gen Virol.* 75, 2271-2276, 1994.
Nardelli-Haefliger et al. "Human Papillomavirus Type 16 Virus-Like Particles Expressed in Attenuated *Salmonella typhimurium* Elicit Mucosal and Systemic Neutralizing Antibodies in Mice". Infect. Immun. 65(8): 3328-3336, 1997.

Roden et al. "In Vitro Generation and Type-Specific Neutralization of a Human Papillomavirus Type 16 Virion Pseudotype" J. Virolology. 70(9): 5875-5883, 1996.
Harper et al. "Efficacy of a bivalent L1 virus-like particle vaccine in prevention of infection with human papillomavirus types 16 and 18 in young women: a randomised controlled trial." Lancet. 364: 1757-1765, 2004.
Harper et al. "Sustained efficacy up to 4•5 years of a bivalent L1 virus-like particle vaccine against human papillomavirus types 16 and 18: follow-up from a randomised control trial." Lancet. 367:1247-1255, 2006.
Garland et al. "Quadrivalent Vaccine against Human Papillomavirus to Prevent Anogenital Diseases." *NEJM.* 356: 1928-1943, 2007.
Paavonen et al. "Efficacy of a prophylactic adjuvanted bivalent L1 virus-like-particle vaccine against infection with human papillomavirus types 16 and 18 in young women: an interim analysis of a phase III double-blind, randomised controlled trial." Lancet 369: 2161-2170, 2007.
Examination Report for Australia patent application No. 2008268014 issued on Sep. 13, 2012.
Examination Report for Malaysia patent application No. PI 20095591 issued on Dec. 31, 2012.
Examination Report for New Zealand patent application No. 582271 issued on Nov. 3, 2010.
International Preliminary Report on Patentability in PCT/JP2008/061569, issued Jul. 29, 2008. English translation dated Jan. 5, 2010.
International Search Report in PCT/JP2006/314919 issued Sep. 5, 2006, with English translation.
Office Action for Japan Application No. 2009-520619 issued on Feb. 5, 2013, with English translation.
Second Official Action for China patent application No. 200880021650.7 issued on Apr. 1, 2013 (with English Translation).
Written Opinion of the ISA in PCT/JP2008/061569, issued Jul. 29, 2008, with English translation.
An Office Action issued on Jun. 2, 2014 in corresponding Philippines Patent Application No. 1/2009/502469.
An Office Action issued on Jul. 28, 2014 in corresponding Canadian Application No. 2,691,745.
A Substantive Examination issued on Jul. 31, 2014 in corresponding Malaysian Application No. PI20095591.
Office Action in corresponding Korean Application No. 2009-7026877 issued on Dec. 10, 2014 (including English translation thereof).
Chinese Office Action for Application No. 200880021650.7, 16 pages (including English language translation), dated Jan. 12, 2015.

* cited by examiner

VACCINE ANTIGEN CAPABLE OF INDUCING CROSS-REACTING AND NEUTRALIZING ANTIBODY AGAINST HIGH-RISK-TYPE HUMAN PAPILLOMAVIRUS

CROSS-REFERENCE TO RELATED APPLICATIONS

This application claims priority from Japanese Patent Application No. 2007-167154 filed on Jun. 26, 2007, and all disclosure therein is incorporated herein by reference.

SEQUENCE LISTING

The instant application contains a Sequence Listing which has been submitted via EFS-Web and is hereby incorporated by reference in its entirety. Said ASCII copy, created on Mar. 11, 2010, is named 5397463.txt, and is 17,288 bytes in size.

TECHNICAL FIELD

The present invention relates to a vaccine antigen inducing cross-reactive neutralizing antibodies to high-risk group human papillomaviruses. In particular, the present invention relates to a chimeric protein composed of human papillomavirus (HPV) 16 L1 protein and a particular human papillomavirus 16 L2 epitope inserted to a particular site thereof and capsid which is an aggregate formed by assembly of the chimeric protein. The capsid according to the present invention is useful as an antigen for use in a vaccine for prevention of infection by human papillomaviruses which may lead to cervical cancer.

BACKGROUND ART

Human papillomavirus (HPV) (FIG. 1) is a small DNA virus, and there are 100 or more genotypes. Fifteen genotypes (high-risk genotypes: 16, 18, 31, 33, 35, 39, 45, 51, 52, 56, 58, 59, 66, 68, and 73) cause cervical cancer. HPV16 is detected in 50 to 60% of cervical cancer. HPV18 is next frequently found in Europe and the United States, while HPV52 and HPV58 are next frequently found in Japan. Although mass examination was carried out for earlier diagnosis in Japan, there are still onset thereof in 15,000 patients and death of 2,500 patients every year.

The HPV capsid has a regular icosahedral skeleton consisting of 72 L1 protein pentamers (capsomeres) and 12 L2 protein molecules bound thereto. The both terminals of the L2 protein are located in the capsid, but part of the N-terminal region is located on the surface of the capsid (L2 surface region) (FIG. 2). Expression of the L1 protein in a great amount by recombinant DNA technique gives virus-like particles (VLPs). Inoculation of the VLP or the L2 protein of bovine or cottontail rabbit papillomavirus makes the inoculated animals resistant to viral challenge. FIG. 2 is a schematic cross-sectional view illustrating the HPV and the VLP.

There is currently no cultured cell line allowing proliferation of the HPV. Pseudoviruses are prepared for monitoring HPV infection. Introduction of a secretory alkali phosphatase (SEAP)-expressing plasmid having the replication origin of SV40, an L1 protein-expressing plasmid, and an L2 protein-expressing plasmid into SV40T antigen-expressing human 293 cell leads to incorporation of the replicated SEAP-expressing plasmid into the L1/L2 capsid, giving an infectious pseudovirus (FIG. 3). The activity of neutralization antibodies is determined by measuring the activity of inhibiting the pseudoviral infection (Nonpatent Document 1).

Each of the antisera obtained by inoculation of the VLP of HPV into animals has a type-specific neutralization activity. Merck developed a vaccine in combination of the VLPs of HPV16 and HPV18 and the VLPs of HPV6 and HPV11, which are possible causes of condyloma acuminatum (benign), while GlaxoSmithKline developed a vaccine in combination of the VLPs of HPV16 and HPV18 (Nonpatent Documents 2 and 3).

These vaccines were shown in large-scale clinical tests to have type-specific infection-preventing action, and the vaccine of Merck was approved in 2006 by FDA and Commission of the European Communities and sold in the U.S and EC countries.

As described above, immunization of the HPV L1 capsid into animals leads to induction of extremely type-specific immune response. Preliminary results in a clinical test by using the HPV16 L1 capsid vaccine showed that the vaccine was effective in preventing HPV16 infection, but almost not effective in preventing other HPV genotypes. Accordingly for prevention of onset of cervical cancer with vaccines, there is a need for development of a vaccine antigen that is effective at least to all high-risk HPVs.

The inventors had earlier developed a vaccine antigen, by using a common neutralization epitope to high-risk HPVs that is present in the amino acid 108-120 region of HPV16 L2 protein. However, the epitope has an amino acid sequence having a homology of about 60 to 75% with high-risk L2 proteins, and the antibody induced thereby bound to multiple high-risk HPVs but was lower in binding efficiency than to HPV 16. Thus, there has been a demand for an antigen having higher type-commonality.

The inventors had found that it was possible to prepare a vaccine antigen capable of inducing a more potent type-common neutralizing antibody by producing a chimeric protein having the HPV16 L1 protein and the amino acid 64-81 region of HPV16 L2 protein inserted thereto and that the vaccine antigen was an antigen having higher type-commonality that was compatible at least with all high-risk HPVs, and filed an patent application (WO2007/018049, Patent Document 1) earlier. Further as described above, in view of the fact that the particles formed of the chimeric protein composed of the HPV 16 L1 protein and an amino acid 108-120 region of HPV16 L2 protein inserted in the HPV16 L1 protein, have strong immunogenicity and potential to induce neutralizing antibody, which is in common to high-risk HPVs, a chimeric protein consisting of the chimeric protein having the additional amino acid 64-81 region inserted by an amino acid 109-117 region of HPV16 L2 protein was provided in Patent Document 1.

Nonpatent Document 1: Pastrana, D.V., Buck, C.B., Pang, Y.Y., Thompson, C.D., Castle, P.E., FitzGerald, D.C., Kruger, Kjaer, S., Lowy, D.R., Schiller, J.T., 2004. Reactivity of human sera in a sensitive, high throughput pseudovirus-based papillomavirus neutralization assay for HPV 16and HPV 18. Virology. 321: 205-216.

Nonpatent Document 2: Villa, L.L., et al.: Prophylactic quadrivalent human papillomavirus types 6, 11, 16, and 18) L1 virus-like particle vaccine in young women: a randomised double-blind placebo-controlled multicentre phase II efficacy trial. Lancet Oncology 6, 271-278, 2005

Nonpatent Document 3: Harper, D.M., et al.: Sustained efficacy up to 4.5 years of a bivalent L1 virus-like particle vaccine against human papillomavirus type 16 and 18: follow up from a randomized control trial. Lancet 367 (9518), 1247-1255.

Patent Document 1: WO2007/018049 All descriptions in the Nonpatent Documents 1 to 3 and Patent Document 1 above are incorporated herein by reference.

HPV vaccines currently commercially available are effective only to HPV16 and HPV18 among 15 high-risk HPVs. Each VLP induces a type-specific neutralizing antibody, and thus, a cocktail of 15 kinds of VLPs are needed for induction of antibodies to all high-risk HPVs, making it difficult to prepare a practical vaccine antigen. Therefore, there is a demand for development of a vaccine antigen that induces a cross-reactive neutralizing antibody.

The antigen described in Patent Document 1 is an antigen compatible at least with all high-risk HPVs that have higher type-commonality. However, it had the following problem. The infectious pseudoviruses used in the study of Patent Document 1 were only HPV16 and HPV18, and the antigen described in Patent Document 1 showed favorable neutralizing activity to these infectious pseudoviruses. However, in the subsequent neutralizing experiment by using HPV31, HPV52 and HPV58 infectious pseudoviruses newly developed by the inventors, the antigen described in Patent Document 1 was lower in neutralizing activity to HPV31, HPV52, and HPV58.

Thus, an object of the present invention is to provide a vaccine antigen capable of inducing a cross-reactive neutralizing antibody to high-risk group human papillomaviruses.

SUMMARY OF THE INVENTION

A first aspect of the present invention is a capsid which is an aggregate formed by assembly of chimeric protein composed of human papillomavirus (HPV) 16 L1 protein and an HPV16 L2 epitope inserted in the loop region of the HPV16 L1 protein, wherein the region for insertion of the L2 epitope is a region of amino acids 430 to 433 and the L2 epitope has an amino acid sequence represented by:
LYKTCKQAGTCPPDIIPKVEG (SEQ ID NO: 2) (hereinafter, referred to as 18-38 L2epitope),
GGLGIGTGSGTGGRTGYIPL (SEQ ID NO: 3) (hereinafter, referred to as 56-75 L2epitope) or
DPVGPLDPSIVSLVEESSFI (SEQ ID NO: 4) (hereinafter, referred to as 96-115 L2epitope).

The capsid according to the present invention includes the following typical embodiments.
1) In the capsid above, the L2 epitope comprises amino acids having said amino acid sequence of which one or more amino acids are deleted or substituted or to which one or more amino acids are added, wherein the amino acids provide the capsid with capability inducing a cross-neutralizing antibody similar to that of the HPV having the original L2 epitope.
2) The aggregate is an aggregate formed by assembly of multiple pentamer capsomeres, each of which composed of five chimeric protein molecules.
3) The an aggregate formed by assembly of multiple pentamer capsomeres has a particle structure.
4) The number of the pentamer capsomeres constituting the aggregate is in the range of 65 to 80.
5) The number of the pentamer capsomeres constituting the aggregate is 72.
6) The capsid is used for production of an L1 capsid vaccine.

A second aspect of the present invention is a capsid mixture comprising two or more kinds of capsids according to the present invention.

The capsid mixtures according to the present invention include the following typical embodiments.

1) The capsid mixture comprises a capsid which is an aggregate formed by assembly of the 18-38 L2 epitope-inserted chimeric protein and a capsid which is an aggregate formed by assembly of the 56-75 L2 epitope-inserted chimeric protein.
2) The capsid mixture comprises a capsid which is an aggregate formed by assembly of the 18-38 L2 epitope-inserted chimeric protein and a capsid which is an aggregate formed by assembly of the 96-115 L2 epitope-inserted chimeric protein.
3) The capsid mixture comprises a capsid which is an aggregate formed by assembly of the 56-75 L2 epitope-inserted chimeric protein and a capsid which is an aggregate formed by assembly of the 96-115 L2 epitope-inserted chimeric protein.
4) The capsid mixture comprises a capsid which is an aggregate formed by assembly of the 18-38 L2 epitope-inserted chimeric protein, a capsid which is an aggregate formed by assembly of the 56-75 L2 epitope-inserted chimeric protein, and a capsid which is an aggregate formed by assembly of the 96-115 L2 epitope-inserted chimeric protein.
5) The capsid mixture is used for production of an L1 capsid vaccine.
6) The capsid mixture is used for production of an L1 capsid vaccine that can induce the neutralizing antibodies at least to human papillomaviruses 16, 18, 31, 52, and 58.

A third aspect of the present invention is a chimeric protein composed of human papillomavirus (HPV) 16 L1 protein and an HPV16 L2epitope inserted in the loop region of the HPV16 L1 protein, wherein the loop region for insertion of the L2 epitope is a region of amino acids 430 to 433, and the L2 epitope has an amino acid sequence represented by:
LYKTCKQAGTCPPDIIPKVEG (SEQ ID NO: 2) (hereinafter, referred to as 18-38 L2epitope),
GGLGIGTGSGTGGRTGYIPL (SEQ ID NO: 3) (hereinafter, referred to as 56-75 L2epitope) or
DPVGPLDPSIVSLVEESSFI (SEQ ID NO: 4) (hereinafter, referred to as 96-115 L2epitope).

In a typical embodiment of the chimeric protein according to the present invention, the L2 epitope is amino acids having said amino acid squence of which one or more Amino acids are deleted or substituted or to which one or more amino acids are added, Wherin the amino acids provide the capsid constituted by the chimeric protein with Capability inducing a cross-neutralizing antibody similar to that of the HPV having the L2 epitope.

A fourth aspect of the present invention is a method of producing the capsid according to the present invention, wherein the capsid is formed by assembly of the chimeric protein above.

A fifth aspect of the present invention is the method of producing the capsid mixture according to the present invention, comprising preparing two or more kinds of capsids by the method according to the method of producing the capsid of the present invention and mixing the resulting capsids.

A sixth aspect of the present invention is a complex of keyhole limpet hemocyanin and human papillomavirus 16 L2 epitope, the L2 epitope having an amino acid sequence represented by:
LYKTCKQAGTCPPDIIPKVEG (SEQ ID NO: 2) (hereinafter, referred to as 18-38 L2epitope),
GGLGIGTGSGTGGRTGYIPL (SEQ ID NO: 3) (hereinafter, referred to as 56-75 L2epitope) or
DPVGPLDPSIVSLVEESSFI (SEQ ID NO: 4) (hereinafter, referred to as 96-115 L2epitope).

In a typical embodiment of the complex according to the present invention, the keyhole limpet hemocyanin and the L2 epitope are bound to each other via cysteine.

The present invention provides an L1 capsid vaccine antigen in which a particle structure has a strong immunoinducing activity, and the L1 capsid vaccine antigen is capable of strong antigen-presenting of the HPV L2 epitope, and which is also capable of inducing a neutralizing antibody, in particular, inducing a neutralizing antibody to HPV16, 18, 31, 52, and 58. Considering the homology of the L2 amino acid sequences in the 15 kinds of high-risk human papillomaviruses described above, the L1 capsid vaccine antigen capable of inducing a neutralizing antibody to HPV16, HPV18, HPV31, HPV52 and HPV58 according to the present invention is quite likely an antigen which can cover almost all of the 15 kinds of high-risk HPVs.

VLP vaccines were already commercialized, and shown to have type-specific infection-preventing action. The chimeric VLP developed by the inventors, which is an antigen consisting of the current vaccine antigen and an additional cross-neutralization L2 epitope, retains the neutralizing epitope of the current vaccine, and thus, induces an HPV16-specific neutralizing antibody and also a cross-reactive neutralizing antibody to HPV18, HPV31, HPV52, and HPV58. The VLP is composed of 360 L1 protein molecules, and thus, the chimeric VLP has 360 cross-neutralization L2 epitopes. It is a new vaccine antigen in a particle structure having a strong immuno inducing activity and presenting the cross-neutralization L2 epitope strongly.

BEST MODE FOR CARRYING OUT THE INVENTION

L1 Capsid

The L1 capsid according to the present invention is a capsid which is an aggregate formed by assembly of chimeric protein composed of human papillomavirus (HPV) 16 L1 protein and a human papillomavirus 16 L2 epitope that is inserted in a loop region of the HPV16 L1 protein.

As described above, HPV particle is a regular icosahedral capsid consisting of 72 capsomeres, each of which contains five L1 protein molecules. High level expression of the L1 protein in cell results in accumulation of the L1 proteins in the nucleus, autonomously forming capsids. The capsid formed only with the L1 proteins is called L1 capsid or virus-like particle (VLP). Simultaneous expression of L1 and L2 proteins gives an L1/L2 capsid (or L1/L2 VLP) containing 12 L2 protein molecules in the L1 capsid. However, the L1 capsid and the L1/L2 capsid are not differentiated from each other by electron microscopy.

The L1 capsid according to the present invention is a capsid based on the HPV16 μl capsid. Because there are many HPV genotypes, each capsid is in principle indicated with a genotype such as HPV16 or HPV58. Thus, for example, the L1 capsid of HPV16 is designated as 16 L1 capsid.

The L1 capsid according to the present invention is an aggregate formed by assembly of chimeric protein, having HPV16 L2 epitopes inserted into the HPV16 L1 protein. Hereinafter, the chimeric protein means a "chimeric protein having an HPV16 L2 epitope inserted into the loop region of the human papillomavirus (HPV) 16 L1 protein," and the present invention includes such chimeric proteins.

The HPV16 L2 epitope inserted into the L1 protein for production of the chimeric protein according to the present invention has an amino acid sequence represented by:

LYKTCKQAGTCPPDIIPKVEG (SEQ ID NO: 2) (18-38 L2 epitope),

GGLGIGTGSGTGGRTGYIPL (SEQ ID NO: 3) (56-75 L2 epitope) or

DPVGPLDPSIVSLVEESSFI (SEQ ID NO: 4) (96-115 L2 epitope).

The 18-38 L2 epitope has 21 amino acids in the 18-38 amino acid region of the HPV16 L2 protein. The 56-75 L2 epitope has 20 amino acids in the 56-75 amino acid region of the HPV16 L2 protein. The 96-115 L2 epitope has 20 amino acids in the 96-115 amino acid region of the HPV16 L2 protein (wherein, the 101st and 112th amino acids are replaced respectively with leucine and serine).

In the present invention, the amino acid residues in protein are numbered from the amino terminal and, for example, the 50th amino acid is designated as amino acid 50.

The L2 surface region binds to multiple cellular proteins. Introduction of amino acid substitution mutation results in loss of infectivity, indicating that the L2 surface region has a function essential for HPV infection (FIG. 4). The amino acid sequence of this region is preserved quite well in all high-risk HPVL2 proteins (FIG. 5). The inventors studied antisera obtained by immunizing rabbits with synthetic peptides having the amino acid sequence in the HPV 16 L2 surface region. The results will be described below in Example (Table 1). The results in Table 1 showed that there are cross-neutralization epitopes in the regions of amino acids 18-38, 49-75, and 96-115.

Specifically, the results shown in Table 1 indicate that there are cross-neutralization epitopes to HPV16, HPV18, HPV31, and HPV58 in the regions of amino acid 18-38, 56-75, and 96-115. However, the cross reactivity to HPV52 was not studied in this stage.

Here, in the 96-115 region, the 101st S was replaced with L, and the 112th T with S. It is because the mutant epitope having L replacing 101st S and S replacing 112th T is superior in inducing cross-reactive antibody to the epitope having the naturally occurring amino acid sequence 96-115.

The results in Table 1 show that there are cross-neutralization epitopes to HPV16, HPV18, HPV31 and HPV58 also in the 49-68 region. However, because the chimeric protein with a 49-75 region including the 49-68 region did not form a particle structure and the homology of L2 amino acids in the 49-55 region was not high in 15 kinds of HPVs as shown in FIG. 5, the 49-68 region was not studied in the present invention.

Thus, chimeric proteins were prepared by inserting the cross-neutralization epitope in the region of amino acids 430 to 433 of L1 protein and chimeric VLPs were produced with the chimeric proteins.

Therefore, the present invention relates to a chimeric protein composed of human papillomavirus (HPV) 16 L1 protein and an HPV16 L2 epitope inserted in the loop region of the HPV16 L1 protein, wherein the loop region for insertion of the L2 epitope is a region of amino acids 430 to 433, and The L2 epitope has an amino acid sequence presented by:

LYKTCKQAGTCPPDIIPKVEG (SEQ ID NO: 2) (hereinafter, referred to as 18-38 L2epitope), GGLGIGTGSGTGGRTGYIPL (SEQ ID NO: 3) (hereinafter, referred to as 56-75 L2epitope) or DPVGPLDPSIVSLVEESSFI (SEQ ID NO: 4) (hereinafter, referred to as 96-115 L2epitope).

The present invention also relates to a capsid which is an aggregate formed by assembly of the chimeric protein. The aggregate is composed of multiple pentamer capsomeres each of which composed of five chimeric protein molecules, and the aggregate composed of the multiple pentamer capsomeres preferably has a particle structure for greater antigenicity. The number of the pentamer capsomeres constituting the particle is, for example, in the range of 65 to 80, preferably 72, which is identical with the number thereof in the naturally occurring viruses.

The naturally occurring VLP generally contains 360 L1 protein molecules and, in such a case, has 360 cross-neutralization epitopes in the particle (FIG. 6). A chimeric protein having a sequence of amino acids 18 to 38, 56 to 75, or 96 to 115 (101st and 112th amino acids replaced respectively with leucine and serine) of HPV16 L2 protein inserted in the region of 430 to 433 of HPV16 L1 protein was expressed in insect sf9 cells by using a recombinant baculovirus, to give a chimeric VLP, which was designated as Ch18/38, Ch56/75, or Ch96/115 (101L, 112S), respectively (FIG. 7). The electron micrograph in FIG. 7 shows the particle structure of respective chimeric VLPs. ELISA by using these chimeric VLPs as antigen showed specific-binding of antibodies to the inserted epitopes to the chimeric VLP (as described below in Table 2 of Example), indicating that the epitopes were exposed on the surface of VLP.

Antisera were prepared by immunizing rabbits with these chimeric VLPs. In ELISA by using a synthetic peptide having the sequence identical with that of the cross-neutralization epitope as an antigen, each antiserum reacted specifically with the inserted epitope. The peptide 96/115 (101L, 112S) aggregated easily, resulting in decrease in the amount bound to the ELISA plate, and thus, the titer obtained was slightly lower (as shown below in Table 3 of Example).

Analysis of the neutralizing activity against HPV16, HPV18, HPV31, HPV52, and HPV58 pseudoviruses showed that: the antibody to Ch18/38 neutralized the HPV16, HPV18 and HPV31; the antibody to Ch56/75, all HPV types; and the antibody to Ch96/115 (101L, 112S), HPV16, HPV18, HPV31 and HPV58 (no neutralization of HPV58 observed with antisera having a low titer) (as shown below in Tables 4 and 5 of Example).

All antisera were found to react intensely with HPV16, the skeleton for the chimeric VLP, indicating that the neutralization epitope inherent to the VLP was conserved in the chimeric VLPs. Because the infectious pseudoviruses consist of 360 L1 protein molecules and 12 L2 protein molecules, the L2 protein excessively produced in the sample is present as liberated in cell. For that reason, the neutralization titer of anti-L2 antibody was obtained rather low.

Animal papillomavirus experiments showed that VLP vaccines and L2 protein vaccines are almost similar in efficacy, indicating that the chimeric VLPs according to the present invention could be practical vaccine antigens inducing generation of antibodies to the cross-neutralization epitopes.

The L2 epitope may be the amino acids having the amino acid sequence above, i.e., that represented by one of the SEQ ID Nos. 2 to 4, of which one or more amino acids are deleted or substituted or to which one or more amino acids are added, wherein the amino acids provide the capsid according to the present invention with capability inducing a cross-neutralizing antibody similar to that of the VLP having the original L2 epitope (having the amino acid sequence represented by any one of the SEQ ID Nos. 2 to 4).

Thus, the 18-38 L2 epitope may include the mutant L2 epitopes of the amino acids having the amino acid sequence represented by LYKTCKQAGTCPPDIIPKVEG (SEQ ID No. 2) of which one or more amino acids are deleted or substituted or to which one or more amino acids are added that provides the capsid according to the present invention with capability inducing a cross-neutralizing antibody similar to that of the HPV16 VLP having the 18-38 L2 epitope.

The capabilites inducing a cross-neutralizing antibody of the HPV16 VLPs having the 18-38 L2 epitope are shown in Table 4.

The 56-75 L2 epitope may include the mutant L2 epitopes of the amino acids having the amino acid sequence represented by GGLGIGTGSGTGGRTGYIPL (SEQ ID No. 3) of which one or more amino acids are deleted or substituted or to which one or more amino acids are added that provides the capsid according to the present invention with capability inducing a cross-neutralizing antibody similar to that of the HPV16 VLP having the 56-75 L2 epitope. The capabilites inducing a cross-neutralizing antibody of the HPV16 VLPs having the 56-75 L2 epitope are shown in Table 4.

Similarly, the 96-115 L2 epitope may include the mutant L2 epitopes of the amino acids having the amino acid sequence represented by DPVGPLDPSIVSLVEESSFI (SEQ ID No. 4) of which one or more amino acids are deleted or substituted or to which one or more amino acids are added that provides the capsid according to the present invention with capability inducing a cross-neutralizing antibody similar to that of the HPV16 VLP having the 96-115 L2 epitope. The capabilites inducing a cross-neutralizing antibody of the HPV16 VLPs having the 96-115 L2 epitope are shown in Table 4. In the present description, the number of the more amino acids in deletion, substitution, or addition is 2, 3, 4, 5, 6, 7, 8, 9 or 10.

The site in the L1 protein of the chimeric protein according to the present invention where the L2 epitope is inserted is in the region of amino acids 430 to 433 of the loop region of L1 protein. Specifically, an L2 epitope of 20 to 21 amino acids is inserted, replacing the four amino acids 430 to 433 in the L1 protein. The amino acid sequence of the HPV16 L1 protein is shown as SEQ ID No. 1. The 426-446 region including amino acids 430 to 433 is estimated to be a region recognizable as the antigen that is located outside the L1 protein, from the viewpoints of structural analysis of HPV16 L1 protein, distribution of neutralizing antibody epitopes, and the position of the cysteine residue essential for capsid formation etc.

The number of the L2 epitopes inserted into the L1 protein is one for a single L1 protein. However, at least two different kinds of L2 epitopes may be inserted into different loop regions in a single L1 protein. For example, a peptide except for the three cross-neutralization epitopes may be inserted to a site except for the amino acids 430 to 433 of L1 protein. Alternatively, one of the three cross-neutralization epitopes may be inserted to a site except for the amino acids 430 to 433 of L1 protein.

(Preparation of L2 Epitope-Containing Peptides)

The L2 peptide (amino acids 18-38, 56-75 or 96-115) can be prepared by a common Fmoc solid-phase method in a 96-column automatic peptide synthesizer. The peptide, which is aimed at preparing an antibody, is connected to KLH (keyhole limpet hemocyanin), and a cysteine residue is added to the N terminal for prevention of masking of the peptide region by KLH.

The present invention includes the complex of keyhole limpet hemocyanin and an HPV16 L2epitope. The L2 epitope has an amino acid sequence represented by:

LYKTCKQAGTCPPDIIPKVEG (SEQ ID NO: 2) (18-38 L2 epitope),

GGLGIGTGSGTGGRTGYIPL (SEQ ID NO: 3) (56-75 L2 epitope) or

DPVGPLDPSIVSLVEESSFI (SEQ ID NO: 4) (96-115 L2 epitope). The keyhole limpet hemocyanin and the L2 epitope are bound to each other preferably via cysteine.

(Preparation of L2 Epitope-Inserted L1 Proteins (Chimeric Proteins))

A chimeric L1 gene was prepared, and the chimeric L1 gene prepared was expressed by using a baculovirus vector, to give a chimeric L1 protein and a chimeric capsid. The chimeric L1 gene is prepared by PCR. Specifically, it is prepared in the following manner:
(A) A primer pair having a region desirably inserted is prepared.
(B) Primer set composed of the primer having an insertion region and the primer 1 and the set composed of the other primer having an insertion region and primer 2 are used for amplification by PCR.
(C) Two amplified DNA fragments having an inserted fragment in one side are prepared. The respective complementary regions are annealed for extension reaction.
(D) A chimeric gene containing the inserted DNA is prepared.
(E) PCR is performed by using the inserted DNA as template and the primers 1 and 2.
(F) Thus, the DNA containing the inserted gene is amplified.

The present invention includes a method of producing a capsid including forming it by an aggregate formed by assembly of the chimeric protein according to the present invention. As described above, a chimeric L1 gene is prepared and expressed by using a baculovirus vector, to give a chimeric L1 protein. The chimeric L1 proteins, once produced, form autonomously a chimeric capsid (the capsid according to the present invention). Expression thereof by using a baculovirus vector may be carried out by a common method, but the condition is preferably optimized for acceleration of the autonomous chimeric capsid formation.

The capsid according to the present invention is used for production of an L1 capsid vaccine. The L1 capsid vaccine may be produced, for example, by using a baculovirus expression system.

The present invention includes capsid mixtures containing two or more kinds of capsids according to the present invention. The three kinds of capsids according to the present invention are different from each other in capability inducing a cross-neutralizing antibody, and use of two or more of these capsids different in capability inducing a cross-neutralizing antibody in combination advantageously gives higher neutralizing activity.

The capsid mixture according to the present invention may be, for example, a mixture of a capsid which is an aggregate formed by assembly of the 18-38 L2 epitope-inserted chimeric protein and a capsid which is an aggregate formed by assembly of the 56-75 L2 epitope-inserted chimeric protein. The two kinds of capsids may be mixed, for example, at a weight ratio in the range of 1:100 to 100:1. However, the mixing ratio of the two kinds of capsids is not limited thereto, and may be modified according to the desired immunogenicity and neutralizing activity of induced antibodies.

The capsid mixture according to the present invention may be, for example, a mixture of a capsid which is an aggregate formed by assembly of the 18-38 L2 epitope-inserted chimeric protein and a capsid which is an aggregate formed by assembly of the 96-115 L2 epitope-inserted chimeric protein. The two kinds of capsids may be mixed, for example, at a weight ratio in the range of 1:100 to 100:1. However, the mixing ratio of the two kinds of capsids is not limited thereto, and may be modified according to the desired immunogenicity and neutralizing activity of induced antibodies.

The capsid mixture according to the present invention may be, for example, a mixture of a capsid which is an aggregate formed by assembly of the 56-75 L2 epitope-inserted chimeric protein and a capsid which is an aggregate formed by assembly of the 96-115 L2 epitope-inserted chimeric protein. The two kinds of capsids may be mixed, for example, at a weight ratio in the range of 1:100 to 100:1. However, the mixing ratio of the two kinds of capsids is not limited thereto, and may be modified according to the desired immunogenicity and neutralizing activity of induced antibodies.

The capsid mixture according to the present invention may be, for example, a mixture of a capsid which is an aggregate formed by assembly of the 18-38 L2 epitope-inserted chimeric protein, a capsid which is an aggregate formed by assembly of the 56-75 L2 epitope-inserted chimeric protein, and a capsid which is an aggregate formed by assembly of the 96-115 L2 epitope-inserted chimeric protein. The three kinds of capsids may be mixed, for example, at a weight ratio between respective two kinds of capsids in the range of 1:100 to 100:1. However, the mixing ratio of the three kinds of capsids is not limited thereto, and may be modified according to the desired immunogenicity and neutralizing activity of induced antibodies.

The capsid mixture according to the present invention is also used for production of the L1 capsid vaccine. The method of producing a vaccine by using the capsid mixture is the same as that described above.

The capsid mixture according to the present invention is used for production of an L1 capsid vaccine that can induce neutralizing antibodies to HPV16, HPV18, HPV31, HPV52 and HPV58.

EXAMPLES

Hereinafter, the present invention will be described in more detail with reference to Examples.

Example 1

Preparation of Rabbit Peptide Antisera

Two Japanese white rabbits (2.5 kg to 3.0 kg) were immunized. The antigen used was a conjugate of a chemically prepared peptide and KLH (keyhole limpet hemocyanin). In the first sensitization, 0.5 mg of the antigen was administered subcutaneously with complete Freund's adjuvant. After two weeks from the first administration, 0.25 mg of the antigen was administered subcutaneously with the complete Freund's adjuvant. The rabbits were sensitized similarly (0.25 mg) additionally after 2, 4, and 6 weeks, cumulatively five times. After one week from the final sensitization, the total blood was collected, to give a serum sample. (The preparation was performed by Scrum Inc. under contract.)

A rabbit was immunized with a synthetic peptide having the amino acid sequence of the HPV16 L2 surface region and the resulting antiserum was analyzed in the neutralization experiment shown below. Results are summarized in Table 1. The results shown in Table 1 show that there are cross-neutralization epitopes in the regions of amino acids 18-38, 49-75, and 96-115.

Neutralization Experiment 1. 293FT cells (purchased from Invitrogen) were inoculated on a 96-well cell culture plate at a concentration of 10,000 cells/well, a day before neutralization experiment.
2. The serum was diluted with a neutralization buffer (DMEM medium without phenol red, containing 10% FCS, 1% non-essential amino acids, 1% L-glutamine acid, and 10 mM HEPES) and mixed with a stock of an infectious pseudovirus, and the mixture was allowed to react at 4° C. for one hour and then added to the 293FT cells inoculated on the previous day.
3. After culture for about 72 hours, 20 μl of the supernatant was collected, and the alkali phosphatase activity thereof was determined according to the method by Roden et al., (see http://home.ccr.cancer.gov/lco/ColorimetricSEAP.htm).

TABLE 1

Neutralizing activity of anti-L2 peptide antibodies

| anti-peptide antibody | HPV16 | HPV18 | HPV31 | HPV58 |
|---|---|---|---|---|
| anti-14/27 | <50 | <50 | <50 | <50 |
|  | <50 | <50 | <50 | <50 |
| anti-18/38 | 800 | 50 | <50 | <50 |
|  | 400 | 100 | <50 | <50 |
| anti-28/42 | <50 | <50 | <50 | <50 |
|  | 800 | <50 | <50 | 50 |
| anti-49/68 | 800 | 50 | 800 | 800 |
| anti-56/75 | 400 | 200 | 200 | 400 |
|  | 200 | 50 | 100 | 200 |
| anti-61/75 | 400 | 100 | <50 | 50 |
|  | 800 | 200 | <50 | 100 |
| anti-64/81 | 3200 | 400 | <50 | 100 |
|  | 800 | 200 | <50 | 50 |
| anti-90/111 | 200 | <50 | 50 | <50 |
|  | 200 | <50 | <50 | <50 |
| anti-96/115 | 200 | <50 | 50 | <50 |
|  | 400 | <50 | 400 | 200 |
| anti-96/115m | 100 | <50 | 200 | 200 |
| (101L, 112S) | 100 | 50 | 100 | 100 |
| anti-107/122 | 100 | <50 | <50 | 50 |
|  | <50 | <50 | <50 | <50 |
| anti-131/144 | 200 | <50 | <50 | <50 |

Example 2

Preparative Method of Capsid Antigen

16 L1 and 16L1/L2 genes were expressed in a recombinant baculovirus system. A recombinant virus was prepared in a Bac-to-Bac baculovirus expression system (GIBCO-BRL Inc., New York, N.Y.), and expressed in Sf9 cells (*Mamestra brassicae*-derived cells). The 16L1 gene was cloned into pFastbac1 vector, to give pFastbac1/16L1. The 16L1/L2 gene was cloned into pFastbac dual vector, to give pFastbac dual/16L1/L2. Then, each cloned pFastbac vector was introduced into DH10BAC *E. coli* (Max efficiency competent cell containing baculovirus DNA and helper plasmid, GIBCO BRL), to give Bacmid. The Bacmid DNA was introduced into the sf-9 cells by using an Effectene Transfection Reagent (QIAGEN GmbH, Hilden, Germany), to give a capsid protein-expressing recombinant baculovirus.

The recombinant baculovirus was infected to sf-9 cells, and the cells were collected after incubation for 72 hours. The infected cells were suspended in 0.5% NP40 solution; the mixture was left still for 10 minutes at room temperature and centrifuged (9000 rpm, 15 minutes, 4° C.), for separation of its nuclear fraction (precipitate) from the cytoplasmic fraction. The nuclear fraction was resuspended in 1.28 g/ml cesium chloride-PBS solution, ultrasonicated for cell destruction (in Sonifier 250, Branson) and ultracentrifuged (34,000 rpm, 20 hours, 20° C.) by using a SW50.1 rotor (Beckman Coulter Inc., Fulleron, Calif.). The protein at a specific density of about 1.28 g/ml in cesium chloride gradient were collected and dialyzed against 0.5 M NaCl—PBS, to give a capsid protein solution.

The sequences of the HPV16 L2 protein amino acids 18 to 38, 56 to 75, or 96 to 115 (101st and 112th amino acids replaced respectively with leucine and serine) were inserted in the region of amino acids 430 to 433 of HPV16 L1 protein by using the method of preparing a capsid antigen, and the resulting chimeric protein was expressed in insect sf9 cells by using a recombinant baculovirus, to give a chimeric VLPs, which were designated respectively as Ch18/38, Ch56/75, and Ch96/115 (101L, 112S). The electron micrograph in FIG. 7 shows the particles of the chimeric VLPs. ELISA by using these chimeric VLPs as antigen showed specific binding of the antibodies to the inserted epitopes, indicating that the epitopes were exposed on the surface of the VLPs.

Measurement Method of Capsid ELISA

1. Each capsid antigen was added in an amount of 1 μg/100 μl/well and the mixture was left at 4° C. overnight.
2. After removal of the antigen solution, 350 μl of blocking solution (5% skim milk in PBS) was added, and the well plate was left still at 37° C. for 2 hours.
3. After removal of the blocking solution, each well was washed with a washing solution (0.05% Teen20/0.05% NP40 in PBS) three times.
4. Fifty μl of the antiserum diluted 500 times with the blocking solution was added to each well, and the solution was left still at room temperature for 1 hour.
5. After removal of the serum sample, the well was washed nine times, and a HRP-bound anti-rabbit IgG antibody diluted 2000 times was added to each well in an amount of 50 μl. The solution is left still at room temperature for 30 minutes, and the well was washed with the washing solution six times after removal of the solution.
6. Fifty μl of a substrate solution (24 mg of o-phenylenediamine dissolved in 12 ml of a citrate-phosphate buffer solution at pH5.0, containing 1.2 μl of $H_2O_2$) was added thereto, and, after color development for 15 minutes, the light intensity at a wavelength of 450 nm was determined by using an Immuno reader.

By using the preparative method for capsid antigen (Example 2), the chimeric proteins, each having the sequences of the amino acids 18 to 38, 56 to 75, or 96 to 115 (101st and 112th amino acids replaced respectively with leucine and serine) of HPV16 L2 protein inserted in the region of the amino acids 430 to 433 of HPV16 L1 protein were expressed in insect sf9 cells by using a recombinant baculovirus, to give chimeric VLPs, which were designated respectively as Ch18/38, Ch56/75, and Ch96/115 (101L, 112S). The electron micrographs in FIG. 7 show the particles of the chimeric VLPs. ELISA by using these chimeric VLPs as antigen showed specific binding of the antibodies to the inserted epitopes to the chimeric VLPs, indicating that the epitopes were exposed on the surface of the VLPs. Results are summarized in Table 2.

TABLE 2

Binding of anti L2-peptide antibodies to chimeric VLP antigen

| antiserum | HPV16 L1VLP | Ch18/38 | Ch56/75 | Ch96/115 (101L, 112S) |
|---|---|---|---|---|
| anti-P18/38 | 0.042 | 0.872 | 0.037 | 0.042 |
| anti-P56/75 | 0.041 | 0.039 | 0.803 | 0.041 |
| anti-P96/115 (101L, 112S) | 0.040 | 0.043 | 0.045 | 0.821 |

(Absorbancy in ELISA with serum diluted at 1 to 500 for the peptide antigens and at 1:2,000 for HPV16 L1VLP)

Antisera were prepared by immunizing rabbits with these chimeric VLPs. The antisera were prepared in a manner similar to Example 1. (However, the dosage of the chimeric capsid was 50 μg, and the adjuvant used was TiterMax (manufactured by TiterMax, U.S.). In ELISA by using a synthetic peptide having the sequence identical with that of the cross-neutralization epitope as an antigen, each antiserum reacted specifically with the inserted epitope. Results are summarized in Table 3. The peptide 96/115 (101L, 112S) aggregated easily, resulting in decrease in the amount bound to the ELISA plate, and thus, the titer obtained was slightly lower than those obtained with other two peptides.

TABLE 3

Binding of anti-chimeric VLP antibodies (serum) to L2-peptide

|  |  | Antigen | | | |
|---|---|---|---|---|---|
|  |  |  | Peptide | | |
| Serum |  | HPV16VLP | P18/38 | P56/75 | P96/115 (101L, 112S) |
| anti-Ch18/38 | #1 | 0.711 | 0.543 | 0.041 | 0.042 |
|  | #2 | 0.633 | 0.402 | 0.039 | 0.039 |
| anti-Ch56/75 | #1 | 0.844 | 0.040 | 0.965 | 0.039 |
|  | #2 | 0.354 | 0.037 | 0.135 | 0.042 |
|  | #3 | 0.923 | 0.043 | 1.034 | 0.045 |
|  | #4 | 0.854 | 0.042 | 0.972 | 0.041 |
| anti-Ch96/115 | #1 | 0.765 | 0.041 | 0.045 | 0.421 (0.170)* |
| (101L, 112S) | #2 | 0.590 | 0.043 | 0.042 | 0.380 (0.158)* |

(Absorbancy in ELISA with serum diluted at 1 to 500 for the peptide antigens and at 1 to 2000 for HPV16VLP)
*indicates the second test result.
Prarenthesis indicate the first test result.

Example 3

Preparation of Infectious Pseudovirus

1. An HPV16 L1 protein-expressing plasmid, an HPV16 L2 protein-expressing plasmid, and a secretory alkali phosphatase-expressing plasmid were transfected to 293TT cells by using Fugene HD. The cells were collected 72 hours after transfection.
2. The collected cells were suspended in a detergent buffer (0.5% Briji58, 0.5% Benzonase and 1% ATP-dependent plasmid safe exonuclease C in D-PBS (CaCl$_2$: 1 mM, MgCl$_2$: 10 mM)) and the suspension was left still at 37° C. overnight.
3. Then, the suspension was left still at 4° C. for 10 minutes, and 5 M NaCl was added thereto to a final NaCl concentration of 850 mM.
4. The cell suspension was centrifuged at 1,500g for 10 minutes, and the supernatant was collected.
5. The collected supernatant was layered on Optiprep (manufactured by AXIS-SHIELD PoC AS) solution at 27%, 33%, or 39% (diluted with PBS), and the solution was ultracentrifuged at 50,000 rpm for 3 hours at 16° C.
6. After ultracentrifugation, each fraction from the bottom face in an amount of about 300 μl was collected, and the fraction having the highest titer was used as the infectious pseudovirus fraction in infection experiment.

Neutralization Experiment 1. 293FT cells (purchased from Invitrogen) were inoculated on a 96-well cell culture plate at a concentration of 10,000 cells/well, a day before neutralization experiment.
2. The serum was diluted with a neutralization buffer (DMEM medium without phenol red, containing 10% FCS, 1% non-essential amino acids, 1% L-glutamine acid, and 10 mM HEPES) and mixed with a stock of an infectious pseudovirus, and the mixture was allowed to react at 4° C. for one hour and then added to the 293FT cells inoculated on the previous day.
3. After culture for about 72 hours, 20 μl of the supernatant was collected, and the alkali phosphatase activity thereof was determined according to the method by Roden et al., (see http://home.ccr.cancer.gov/lco/ColorimetricSEAP.htm).

The neutralizing activities of anti-chimeric VLP antibodies against the HPV16, HPV18, HPV31, HPV35, HPV52, and HPV58 pseudoviruses were studied by using the method above. Results are summarized in Table 4. The antibody to Ch18/38 neutralized the HPV16, HPV18 and HPV31 pseudoviruses. The antibody to Ch56/75 neutralized all six kinds of pseudoviruses. The antibody to Ch96/115 (101L, 112S) neutralized the HPV16, HPV18, HPV31 and HPV58 pseudoviruses (neutralization of low-titer antisera was not observed with the HPV58 pseudovirus). The anti-HPV16 VLP for comparison neutralized the HPV16, HPV31 and HPV35 pseudoviruses.

TABLE 4

Neutralization of HPV16, HPV18, HPV31, HPV52, and HPV58 pseudoviruses by anti-chimeric VLP serum

|  |  | Neutralization titer | | | | | |
|---|---|---|---|---|---|---|---|
| Serum |  | HPV16 | HPV18 | HPV31 | HPV35 | HPV52 | HPV58 |
| anti-Ch18/38 | #1 | 204,800 | 400 | 3,200 | NT | <50 | <50 |
|  | #2 | 102,400 | 200 | 50 | NT | <50 | <50 |
| anti-Ch56/75 | #1 | 51,200 | 200 | 3,200 | 6,400 | 6,400 | 1,600 |
|  | #2 | 1,600 | <50 | 50 | 400 | 400 | 50 |
|  | #3 | 51,200 | 800 | 50 | 100 | 50 | 400 |
|  | #4 | 409,600 | 100 | 800 | 50 | 6,400 | 400 |
|  | #5 | 204,800 | 100 | 3200 | NT | 3,200 | 800 |
| anti-Ch96/115 | #1 | 204,800 | 100 | 800 | NT | <50 | 50 |
| (101L, 112S) | #2 | 102,400 | 50 | 50 | NT | <50 | <50 |
| anti-HPV16VLP |  | 204,800 | <50 | 800 | 50 | <50 | <50 |

In addition, the neutralizing activities of the antibody mixtures (weight ratio: 1:1) to the HPV16, HPV18, HPV31, HPV52, and HPV58 pseudoviruses were studied. Results are summarized in Table 5. The mixture of the antibodies to Ch18/38 and Ch56/75 and the mixture of the antibodies to Ch56/75 and Ch96/115 (101L, 112S) neutralized all five types of pseudoviruses. The mixture of the antibodies to Ch18/38 and Ch96/115 (101L, 112S) neutralized HPV16, HPV18, HPV31 and HPV58 pseudoviruses.

TABLE 5

Neutralizing activity of anti chimeric VLP antibodies

| Mixture of antisera | Neutralizing titer | | | | |
|---|---|---|---|---|---|
| | HPV16 | HPV18 | HPV31 | HPV52 | HPV58 |
| anti-Ch18/38 #1 anti-Ch56/78 #1 | 204,800 | 800 | 3,200 | 3,200 | 400 |
| anti-Ch56/78 #1 anti-Ch96/115 (101L, 112S) #1 | 204,800 | 200 | 3,200 | 3,200 | 400 |
| anti-Ch18/38 #1 anti-Ch96/115 (101L, 112S) #1 | 204,800 | 200 | 1,600 | <50 | 50 |

The following literatures may be referred to, in performing the experiments in the Examples of the present description. The following literatures and all disclosures therein are incorporated herein by reference.

REFERENCE LITERATURES

1) Matsumoto. K, et al.: Antibodies to human papillomavirus 16, 18, 58, and 6b major capsid proteins among Japanese females. Jpn. J. Cancer Res., 88, 369-375, 1997.
2) Xiaojiang S. Chen, et al.: Structure of small virus-like particles assembled from the L1 protein of human papillomavirus 16. Mol. Cell., 5, 557-567, 2000.
3) Jean-Remy Sadeyen, et al.: Insertion of a foreign sequence on capsid surface loops of human papillomavirus type 16 virus-like particles reduces their capacity to induce neutralizing antibodies and delineates a conformational neutralizing epitope. Virology., 309, 32-40, 2003.
4) Ishii. Y, et al.: Mutational analysis of human papillomavirus type 16 major capsid protein L1: the cysteines affecting the intermolecular bonding and structure of L1 capsids. Virology., 308, 128-136, 2003.

INDUSTRIAL APPLICABILITY

The capsid according to the present invention is an antigen of HPV16 VLP having an additional L2 type-common epitope. The capsid contains additional 360 new epitopes in a particle, while retaining its antigenicity of current vaccines. After verification tests of the infection-preventing activity with the anti-L2 antibody, it can be used as a vaccine antigen that may possibly prevent infection of all carcinogenic HPVs. It is possibly a second-generation HPV vaccine antigen that can prevent infection of high-risk HPV-related diseases, such as cervical cancer, which accounts for about 11% of the world female malignant tumors (450 thousand patients).

BRIEF DESCRIPTION OF THE DRAWINGS

FIG. 5 disclosed the sequences in the left column as SEQ ID NOS 2 and 5-18, the middle column as SEQ ID NOS 19-33 and the right column as SEQ ID NOS 34-48, respectively, in order of appearance.

SEQUENCE LISTING

Figure 1:
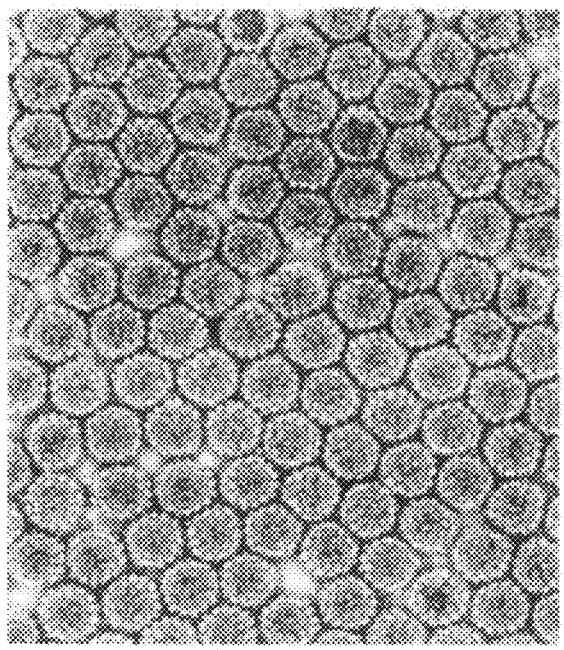
FIG. 1 is an illustration for explaining human papillomavirus particles. Genome: double-stranded circular DNA, Particle: regular icosahedral (55 nm), Various mammals are persistently infected with papillomaviruses specific to each species. There are 100 or more HPV types, and infection of 15 types thereof (in high-risk group) causes onset of cervical cancer.
Figure 2:
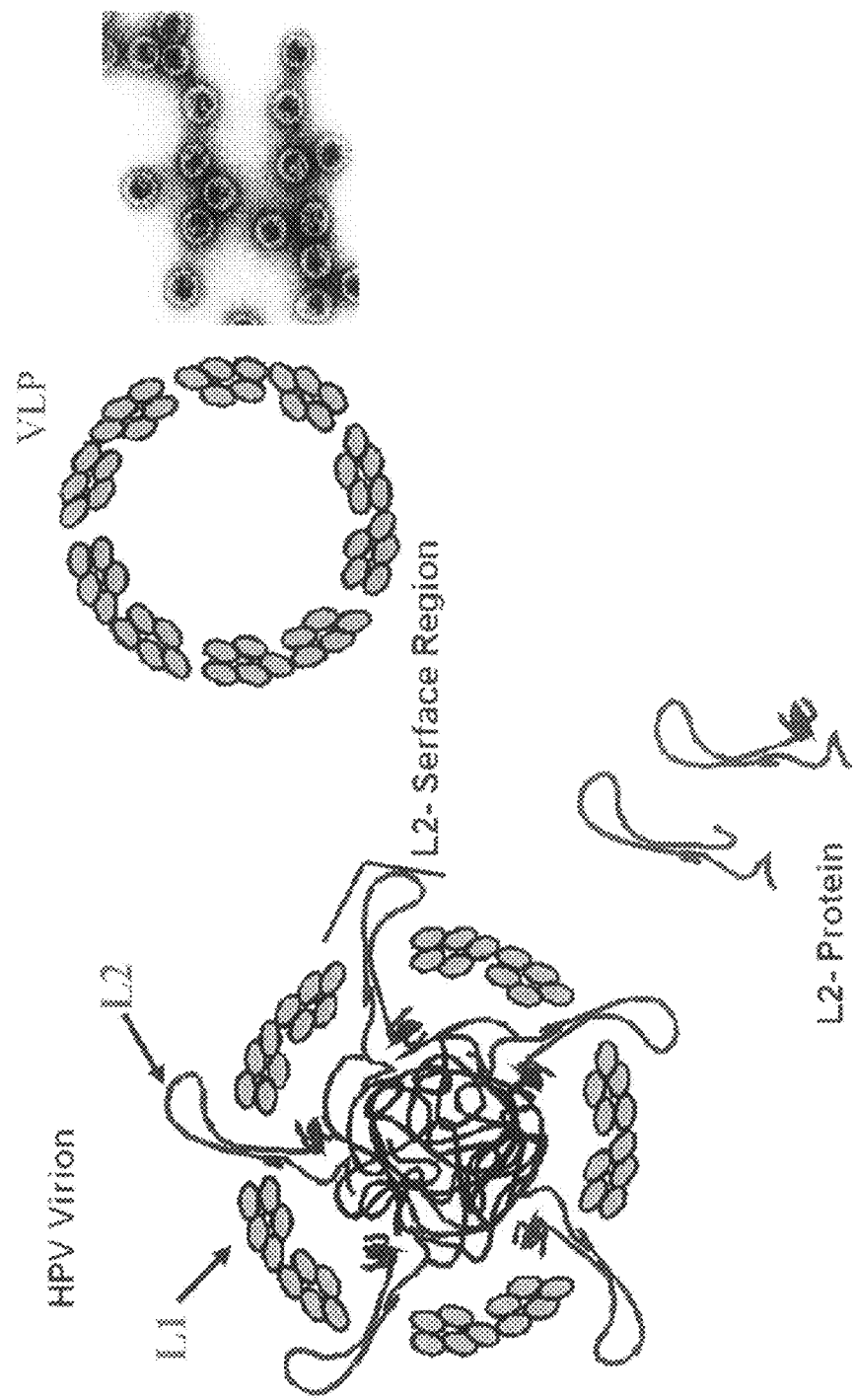
FIG. 2 are views explaining the virus-like particle (VLP). There is practically no cultured cell. line allowing proliferation of the HPV. Expression of the L1 protein for example with a recombinant baculovirus results in assembly thereof in the nucleus, forming VLPs. First-generation vaccines contain a type 16 or 18 VLP as an antigen. The antigenicity of VLPs is highly type-specific.
Figure 3:
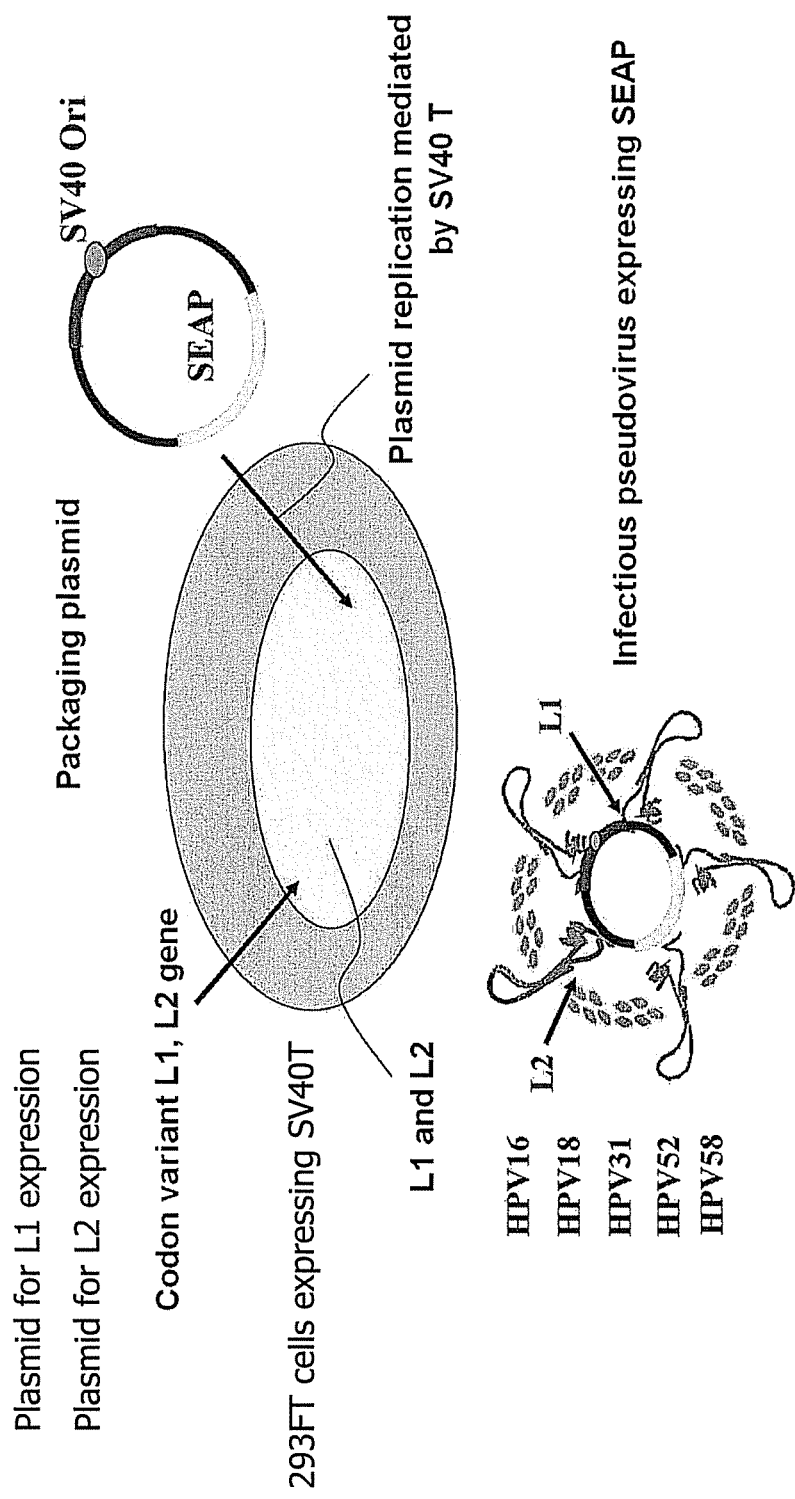
FIG. 3 is a drawing explaining the preparative method for an infectious pseudovirus.
Figure 4:
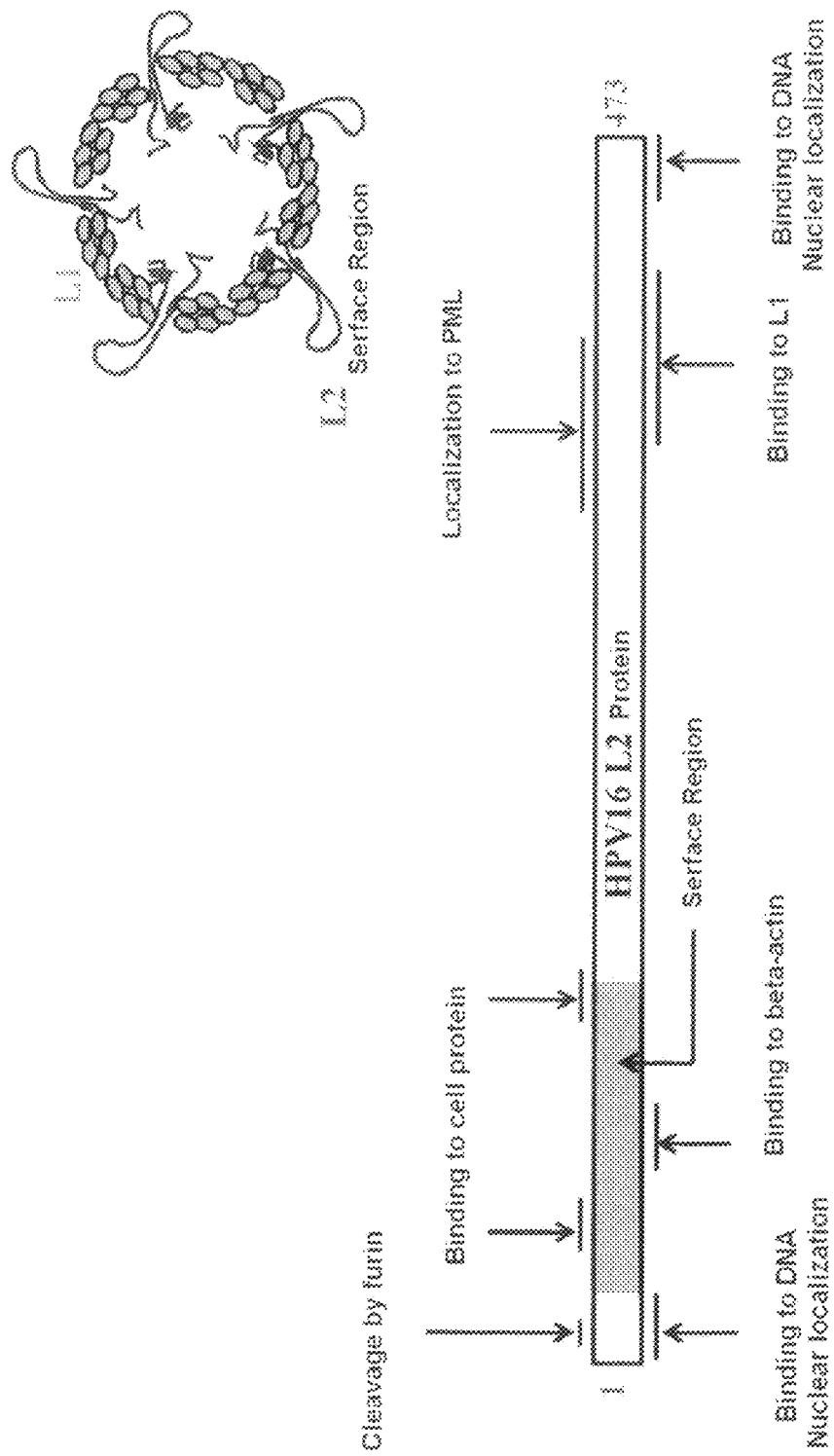
FIG. 4 is a drawing explaining the L2 surface region. The amino acid sequence in the L2 surface region of carcinogenic HPV, highly homologous in amino acid sequences, plays an essential role in infectivity of HPVs.
Figure 5:
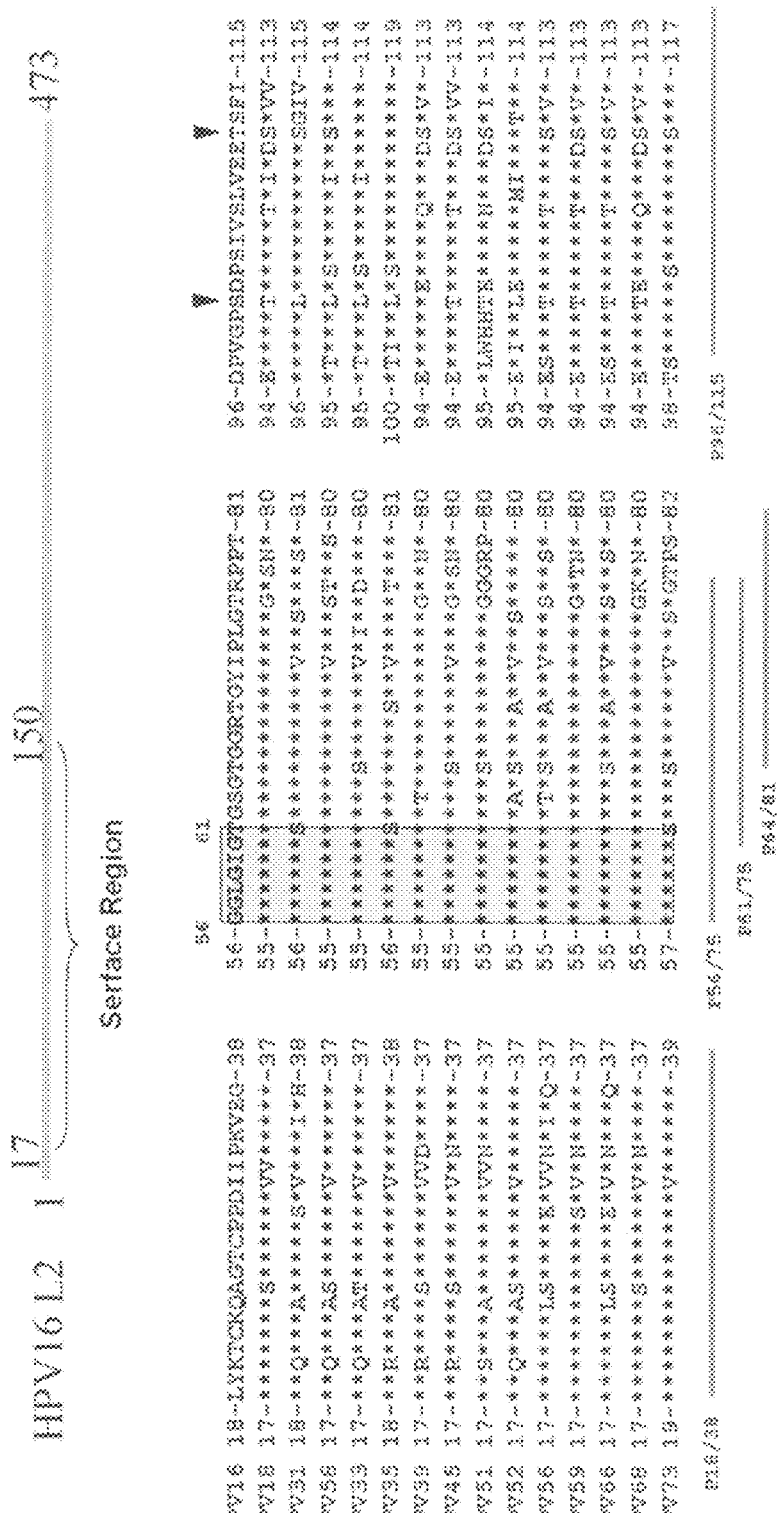
FIG. 5 shows the amino acid sequence of the L2 surface region of HPV16.
Figure 6:
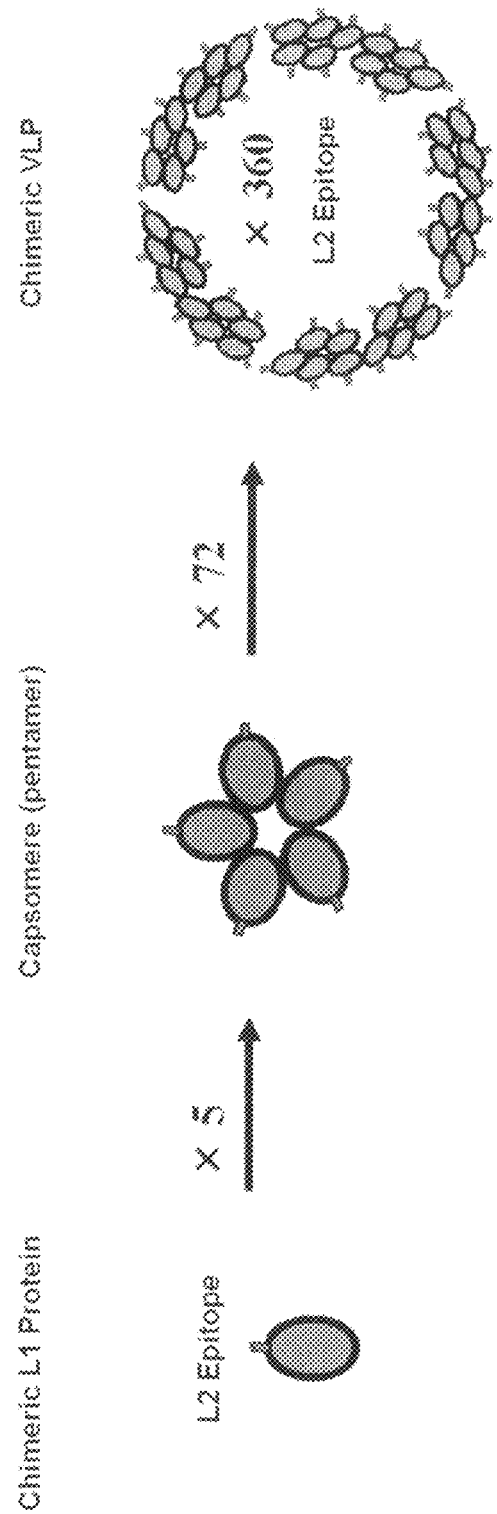
FIG. 6 is a drawing explaining the chimeric VLP prepared by inserting cross-neutralization epitope into the L1 protein. The Chimeric VLP has 360 cross-neutralization L2 epitopes. The antigenicity and the stability of the VLP were verified.
Figure 7:
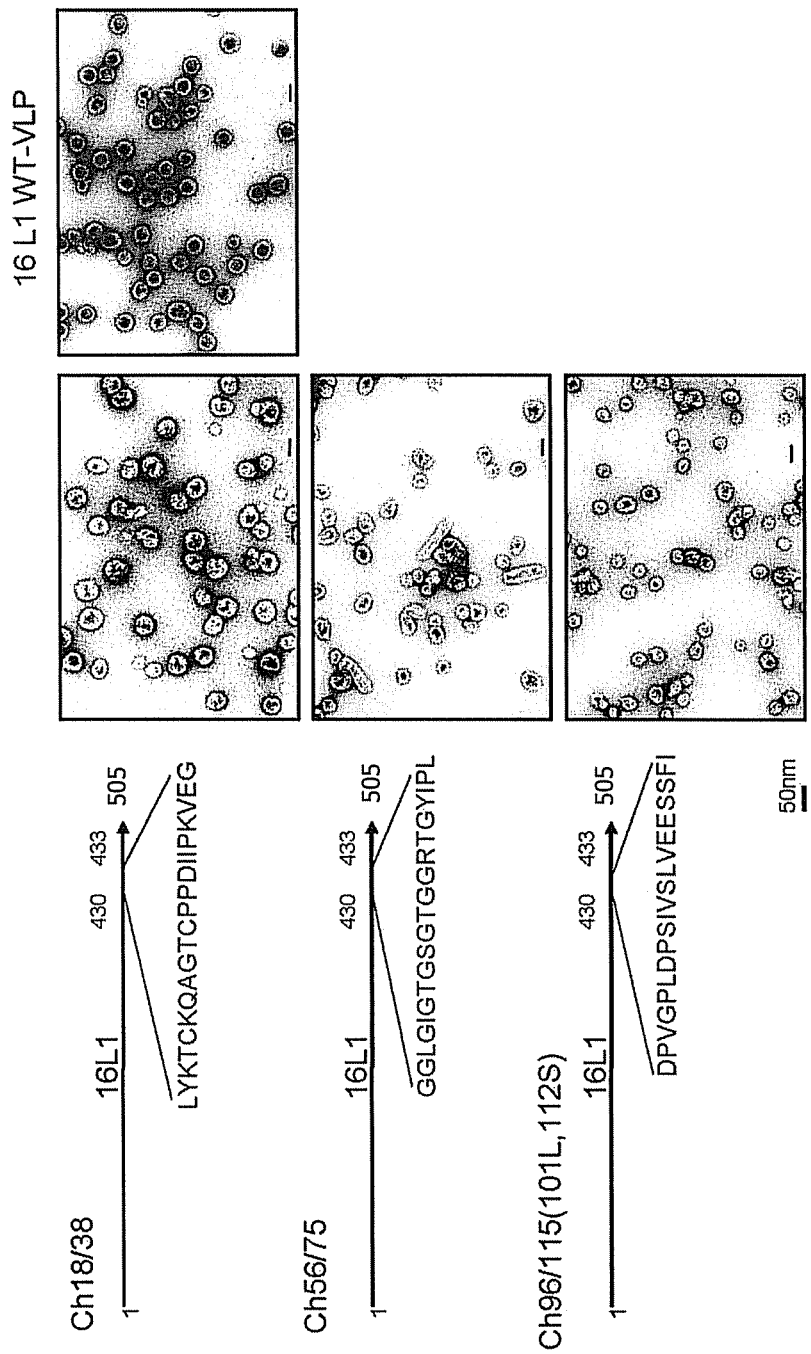
FIG. 7 includes drawings explaining chimeric VLPs, Ch18/38, Ch56/75 and Ch96/115 (101L, 112S) (including amino acid sequences (SEQ ID NOS 2-4, respectively, in order of appearance)) and photographs of the particles. 16 L1 WT-VLP is a photograph of non-chimeric VLP.

```
<160> NUMBER OF SEQ ID NOS: 48

<210> SEQ ID NO 1
<211> LENGTH: 505
<212> TYPE: PRT
<213> ORGANISM: Human papilloma virus

<400> SEQUENCE: 1

Met Ser Leu Trp Leu Pro Ser Glu Ala Thr Val Tyr Leu Pro Pro Val
1               5                   10                  15

Pro Val Ser Lys Val Val Ser Thr Asp Glu Tyr Val Ala Arg Thr Asn
                20                  25                  30

Ile Tyr Tyr His Ala Gly Thr Ser Arg Leu Leu Ala Val Gly His Pro
            35                  40                  45

Tyr Phe Pro Ile Lys Lys Pro Asn Asn Asn Lys Ile Leu Val Pro Lys
        50                  55                  60
```

```
Val Ser Gly Leu Gln Tyr Arg Val Phe Arg Ile His Leu Pro Asp Pro
 65                  70                  75                  80

Asn Lys Phe Gly Phe Pro Asp Thr Ser Phe Tyr Asn Pro Asp Thr Gln
                 85                  90                  95

Arg Leu Val Trp Ala Cys Val Gly Val Glu Val Gly Arg Gly Gln Pro
            100                 105                 110

Leu Gly Val Gly Ile Ser Gly His Pro Leu Leu Asn Lys Leu Asp Asp
        115                 120                 125

Thr Glu Asn Ala Ser Ala Tyr Ala Ala Asn Ala Gly Val Asp Asn Arg
    130                 135                 140

Glu Cys Ile Ser Met Asp Tyr Lys Gln Thr Gln Leu Cys Leu Ile Gly
145                 150                 155                 160

Cys Lys Pro Pro Ile Gly Glu His Trp Gly Lys Gly Ser Pro Cys Thr
                165                 170                 175

Asn Val Ala Val Asn Pro Gly Asp Cys Pro Pro Leu Glu Leu Ile Asn
            180                 185                 190

Thr Val Ile Gln Asp Gly Asp Met Val Asp Thr Gly Phe Gly Ala Met
        195                 200                 205

Asp Phe Thr Thr Leu Gln Ala Asn Lys Ser Glu Val Pro Leu Asp Ile
    210                 215                 220

Cys Thr Ser Ile Cys Lys Tyr Pro Asp Tyr Ile Lys Met Val Ser Glu
225                 230                 235                 240

Pro Tyr Gly Asp Ser Leu Phe Phe Tyr Leu Arg Arg Glu Gln Met Phe
                245                 250                 255

Val Arg His Leu Phe Asn Arg Ala Gly Thr Val Gly Glu Asn Val Pro
            260                 265                 270

Asp Asp Leu Tyr Ile Lys Gly Ser Gly Ser Thr Ala Asn Leu Ala Ser
        275                 280                 285

Ser Asn Tyr Phe Pro Thr Pro Ser Gly Ser Met Val Thr Ser Asp Ala
290                 295                 300

Gln Ile Phe Asn Lys Pro Tyr Trp Leu Gln Arg Ala Gln Gly His Asn
305                 310                 315                 320

Asn Gly Ile Cys Trp Gly Asn Gln Leu Phe Val Thr Val Val Asp Thr
                325                 330                 335

Thr Arg Ser Thr Asn Met Ser Leu Cys Ala Ala Ile Ser Thr Ser Glu
            340                 345                 350

Thr Thr Tyr Lys Asn Thr Asn Phe Lys Glu Tyr Leu Arg His Gly Glu
        355                 360                 365

Glu Tyr Asp Leu Gln Phe Ile Phe Gln Leu Cys Lys Ile Thr Leu Thr
    370                 375                 380

Ala Asp Val Met Thr Tyr Ile His Ser Met Asn Ser Thr Ile Leu Glu
385                 390                 395                 400

Asp Trp Asn Phe Gly Leu Gln Pro Pro Gly Gly Thr Leu Glu Asp
                405                 410                 415

Thr Tyr Arg Phe Val Thr Ser Gln Ala Ile Ala Cys Gln Lys His Thr
            420                 425                 430

Pro Pro Ala Pro Lys Glu Asp Pro Leu Lys Lys Tyr Thr Phe Trp Glu
        435                 440                 445

Val Asn Leu Lys Glu Lys Phe Ser Ala Asp Leu Asp Gln Phe Pro Leu
    450                 455                 460

Gly Arg Lys Phe Leu Leu Gln Ala Gly Leu Lys Ala Lys Pro Lys Phe
465                 470                 475                 480
```

```
Thr Leu Gly Lys Arg Lys Ala Thr Pro Thr Ser Ser Thr Ser Thr
                485                 490                 495
Thr Ala Lys Arg Lys Lys Arg Lys Leu
            500                 505

<210> SEQ ID NO 2
<211> LENGTH: 21
<212> TYPE: PRT
<213> ORGANISM: Human papilloma virus

<400> SEQUENCE: 2

Leu Tyr Lys Thr Cys Lys Gln Ala Gly Thr Cys Pro Pro Asp Ile Ile
1               5                   10                  15

Pro Lys Val Glu Gly
            20

<210> SEQ ID NO 3
<211> LENGTH: 20
<212> TYPE: PRT
<213> ORGANISM: Human papilloma virus

<400> SEQUENCE: 3

Gly Gly Leu Gly Ile Gly Thr Gly Ser Gly Thr Gly Gly Arg Thr Gly
1               5                   10                  15

Tyr Ile Pro Leu
            20

<210> SEQ ID NO 4
<211> LENGTH: 20
<212> TYPE: PRT
<213> ORGANISM: Human papilloma virus

<400> SEQUENCE: 4

Asp Pro Val Gly Pro Leu Asp Pro Ser Ile Val Ser Leu Val Glu Glu
1               5                   10                  15

Ser Ser Phe Ile
            20

<210> SEQ ID NO 5
<211> LENGTH: 21
<212> TYPE: PRT
<213> ORGANISM: Human papilloma virus

<400> SEQUENCE: 5

Leu Tyr Lys Thr Cys Lys Gln Ser Gly Thr Cys Pro Pro Asp Val Val
1               5                   10                  15

Pro Lys Val Glu Gly
            20

<210> SEQ ID NO 6
<211> LENGTH: 21
<212> TYPE: PRT
<213> ORGANISM: Human papilloma virus

<400> SEQUENCE: 6

Leu Tyr Gln Thr Cys Lys Ala Ala Gly Thr Cys Pro Ser Asp Val Ile
1               5                   10                  15

Pro Lys Ile Glu His
            20
```

```
<210> SEQ ID NO 7
<211> LENGTH: 21
<212> TYPE: PRT
<213> ORGANISM: Human papilloma virus

<400> SEQUENCE: 7

Leu Tyr Gln Thr Cys Lys Ala Ser Gly Thr Cys Pro Pro Asp Val Ile
1               5                   10                  15

Pro Lys Val Glu Gly
            20

<210> SEQ ID NO 8
<211> LENGTH: 21
<212> TYPE: PRT
<213> ORGANISM: Human papilloma virus

<400> SEQUENCE: 8

Leu Tyr Gln Thr Cys Lys Ala Thr Gly Thr Cys Pro Pro Asp Val Ile
1               5                   10                  15

Pro Lys Val Glu Gly
            20

<210> SEQ ID NO 9
<211> LENGTH: 21
<212> TYPE: PRT
<213> ORGANISM: Human papilloma virus

<400> SEQUENCE: 9

Leu Tyr Arg Thr Cys Lys Ala Ala Gly Thr Cys Pro Pro Asp Val Ile
1               5                   10                  15

Pro Lys Val Glu Gly
            20

<210> SEQ ID NO 10
<211> LENGTH: 21
<212> TYPE: PRT
<213> ORGANISM: Human papilloma virus

<400> SEQUENCE: 10

Leu Tyr Arg Thr Cys Lys Gln Ser Gly Thr Cys Pro Pro Asp Val Val
1               5                   10                  15

Asp Lys Val Glu Gly
            20

<210> SEQ ID NO 11
<211> LENGTH: 21
<212> TYPE: PRT
<213> ORGANISM: Human papilloma virus

<400> SEQUENCE: 11

Leu Tyr Arg Thr Cys Lys Gln Ser Gly Thr Cys Pro Pro Asp Val Ile
1               5                   10                  15

Asn Lys Val Glu Gly
            20

<210> SEQ ID NO 12
<211> LENGTH: 21
<212> TYPE: PRT
<213> ORGANISM: Human papilloma virus
```

<400> SEQUENCE: 12

Leu Tyr Ser Thr Cys Lys Ala Ala Gly Thr Cys Pro Pro Asp Val Val
1               5                   10                  15

Asn Lys Val Glu Gly
            20

<210> SEQ ID NO 13
<211> LENGTH: 21
<212> TYPE: PRT
<213> ORGANISM: Human papilloma virus

<400> SEQUENCE: 13

Leu Tyr Gln Thr Cys Lys Ala Ser Gly Thr Cys Pro Pro Asp Val Ile
1               5                   10                  15

Pro Lys Val Glu Gly
            20

<210> SEQ ID NO 14
<211> LENGTH: 21
<212> TYPE: PRT
<213> ORGANISM: Human papilloma virus

<400> SEQUENCE: 14

Leu Tyr Lys Thr Cys Lys Leu Ser Gly Thr Cys Pro Glu Asp Val Val
1               5                   10                  15

Asn Lys Ile Glu Gln
            20

<210> SEQ ID NO 15
<211> LENGTH: 21
<212> TYPE: PRT
<213> ORGANISM: Human papilloma virus

<400> SEQUENCE: 15

Leu Tyr Lys Thr Cys Lys Gln Ala Gly Thr Cys Pro Ser Asp Val Ile
1               5                   10                  15

Asn Lys Val Glu Gly
            20

<210> SEQ ID NO 16
<211> LENGTH: 21
<212> TYPE: PRT
<213> ORGANISM: Human papilloma virus

<400> SEQUENCE: 16

Leu Tyr Lys Thr Cys Lys Leu Ser Gly Thr Cys Pro Glu Asp Val Ile
1               5                   10                  15

Asn Lys Val Glu Gln
            20

<210> SEQ ID NO 17
<211> LENGTH: 21
<212> TYPE: PRT
<213> ORGANISM: Human papilloma virus

<400> SEQUENCE: 17

Leu Tyr Lys Thr Cys Lys Gln Ser Gly Thr Cys Pro Pro Asp Val Ile
1               5                   10                  15

Asn Lys Val Glu Gly
            20

<210> SEQ ID NO 18
<211> LENGTH: 21
<212> TYPE: PRT
<213> ORGANISM: Human papilloma virus

<400> SEQUENCE: 18

Leu Tyr Lys Thr Cys Lys Gln Ala Gly Thr Cys Pro Pro Asp Val Ile
1               5                   10                  15

Pro Lys Val Glu Gly
            20

<210> SEQ ID NO 19
<211> LENGTH: 26
<212> TYPE: PRT
<213> ORGANISM: Human papilloma virus

<400> SEQUENCE: 19

Gly Gly Leu Gly Ile Gly Thr Gly Ser Gly Thr Gly Gly Arg Thr Gly
1               5                   10                  15

Tyr Ile Pro Leu Gly Thr Arg Pro Pro Thr
            20                  25

<210> SEQ ID NO 20
<211> LENGTH: 26
<212> TYPE: PRT
<213> ORGANISM: Human papilloma virus

<400> SEQUENCE: 20

Gly Gly Leu Gly Ile Gly Thr Gly Ser Gly Thr Gly Gly Arg Thr Gly
1               5                   10                  15

Tyr Ile Pro Leu Gly Gly Arg Ser Asn Thr
            20                  25

<210> SEQ ID NO 21
<211> LENGTH: 26
<212> TYPE: PRT
<213> ORGANISM: Human papilloma virus

<400> SEQUENCE: 21

Gly Gly Leu Gly Ile Gly Ser Gly Ser Gly Thr Gly Gly Arg Thr Gly
1               5                   10                  15

Tyr Val Pro Leu Ser Thr Arg Pro Ser Thr
            20                  25

<210> SEQ ID NO 22
<211> LENGTH: 26
<212> TYPE: PRT
<213> ORGANISM: Human papilloma virus

<400> SEQUENCE: 22

Gly Gly Leu Gly Ile Gly Thr Gly Ser Gly Thr Gly Gly Arg Thr Gly
1               5                   10                  15

Tyr Val Pro Leu Gly Ser Thr Pro Pro Ser
            20                  25

<210> SEQ ID NO 23
<211> LENGTH: 26
<212> TYPE: PRT
<213> ORGANISM: Human papilloma virus

<400> SEQUENCE: 23

Gly Gly Leu Gly Ile Gly Thr Gly Ser Gly Ser Gly Gly Arg Thr Gly
1               5                   10                  15

Tyr Val Pro Ile Gly Thr Asp Pro Pro Thr
            20                  25

<210> SEQ ID NO 24
<211> LENGTH: 26
<212> TYPE: PRT
<213> ORGANISM: Human papilloma virus

<400> SEQUENCE: 24

Gly Gly Leu Gly Ile Gly Ser Gly Ser Gly Thr Gly Gly Arg Ser Gly
1               5                   10                  15

Tyr Val Pro Leu Gly Thr Thr Pro Pro Thr
            20                  25

<210> SEQ ID NO 25
<211> LENGTH: 26
<212> TYPE: PRT
<213> ORGANISM: Human papilloma virus

<400> SEQUENCE: 25

Gly Gly Leu Gly Ile Gly Thr Gly Thr Gly Thr Gly Gly Arg Thr Gly
1               5                   10                  15

Tyr Ile Pro Leu Gly Gly Arg Pro Asn Thr
            20                  25

<210> SEQ ID NO 26
<211> LENGTH: 26
<212> TYPE: PRT
<213> ORGANISM: Human papilloma virus

<400> SEQUENCE: 26

Gly Gly Leu Gly Ile Gly Thr Gly Ser Gly Ser Gly Gly Arg Thr Gly
1               5                   10                  15

Tyr Val Pro Leu Gly Gly Arg Ser Asn Thr
            20                  25

<210> SEQ ID NO 27
<211> LENGTH: 26
<212> TYPE: PRT
<213> ORGANISM: Human papilloma virus

<400> SEQUENCE: 27

Gly Gly Leu Gly Ile Gly Thr Gly Ser Gly Ser Gly Gly Arg Thr Gly
1               5                   10                  15

Tyr Ile Pro Leu Gly Gly Gly Gly Arg Pro
            20                  25

<210> SEQ ID NO 28
<211> LENGTH: 26
<212> TYPE: PRT
<213> ORGANISM: Human papilloma virus

<400> SEQUENCE: 28

Gly Gly Leu Gly Ile Gly Thr Gly Ala Gly Ser Gly Gly Arg Ala Gly
1               5                   10                  15

Tyr Val Pro Leu Ser Thr Arg Pro Pro Thr
            20                  25

```
<210> SEQ ID NO 29
<211> LENGTH: 26
<212> TYPE: PRT
<213> ORGANISM: Human papilloma virus

<400> SEQUENCE: 29

Gly Gly Leu Gly Ile Gly Thr Gly Thr Gly Ser Gly Gly Arg Ala Gly
1               5                   10                  15

Tyr Val Pro Leu Gly Ser Arg Pro Ser Thr
            20                  25

<210> SEQ ID NO 30
<211> LENGTH: 26
<212> TYPE: PRT
<213> ORGANISM: Human papilloma virus

<400> SEQUENCE: 30

Gly Gly Leu Gly Ile Gly Thr Gly Ser Gly Thr Gly Gly Arg Thr Gly
1               5                   10                  15

Tyr Ile Pro Leu Gly Gly Arg Thr Asn Thr
            20                  25

<210> SEQ ID NO 31
<211> LENGTH: 26
<212> TYPE: PRT
<213> ORGANISM: Human papilloma virus

<400> SEQUENCE: 31

Gly Gly Leu Gly Ile Gly Thr Gly Ser Gly Ser Gly Gly Arg Ala Gly
1               5                   10                  15

Tyr Val Pro Leu Gly Ser Arg Pro Ser Thr
            20                  25

<210> SEQ ID NO 32
<211> LENGTH: 26
<212> TYPE: PRT
<213> ORGANISM: Human papilloma virus

<400> SEQUENCE: 32

Gly Gly Leu Gly Ile Gly Thr Gly Ser Gly Thr Gly Gly Arg Thr Gly
1               5                   10                  15

Tyr Ile Pro Leu Gly Gly Lys Pro Asn Thr
            20                  25

<210> SEQ ID NO 33
<211> LENGTH: 26
<212> TYPE: PRT
<213> ORGANISM: Human papilloma virus

<400> SEQUENCE: 33

Gly Gly Leu Gly Ile Gly Ser Gly Ser Gly Ser Gly Gly Arg Thr Gly
1               5                   10                  15

Tyr Val Pro Leu Ser Thr Gly Thr Pro Ser
            20                  25

<210> SEQ ID NO 34
<211> LENGTH: 20
<212> TYPE: PRT
<213> ORGANISM: Human papilloma virus
```

```
<400> SEQUENCE: 34

Asp Pro Val Gly Pro Ser Asp Pro Ser Ile Val Ser Leu Val Glu Glu
1               5                   10                  15

Thr Ser Phe Ile
            20

<210> SEQ ID NO 35
<211> LENGTH: 20
<212> TYPE: PRT
<213> ORGANISM: Human papilloma virus

<400> SEQUENCE: 35

Glu Pro Val Gly Pro Thr Asp Pro Ser Ile Val Thr Leu Ile Glu Asp
1               5                   10                  15

Ser Ser Val Val
            20

<210> SEQ ID NO 36
<211> LENGTH: 20
<212> TYPE: PRT
<213> ORGANISM: Human papilloma virus

<400> SEQUENCE: 36

Asp Pro Val Gly Pro Leu Asp Pro Ser Ile Val Ser Leu Val Glu Glu
1               5                   10                  15

Ser Gly Ile Val
            20

<210> SEQ ID NO 37
<211> LENGTH: 20
<212> TYPE: PRT
<213> ORGANISM: Human papilloma virus

<400> SEQUENCE: 37

Asp Thr Val Gly Pro Leu Asp Ser Ser Ile Val Ser Leu Ile Glu Glu
1               5                   10                  15

Ser Ser Phe Ile
            20

<210> SEQ ID NO 38
<211> LENGTH: 20
<212> TYPE: PRT
<213> ORGANISM: Human papilloma virus

<400> SEQUENCE: 38

Asp Thr Val Gly Pro Leu Asp Ser Ser Ile Val Ser Leu Ile Glu Glu
1               5                   10                  15

Thr Ser Phe Ile
            20

<210> SEQ ID NO 39
<211> LENGTH: 20
<212> TYPE: PRT
<213> ORGANISM: Human papilloma virus

<400> SEQUENCE: 39

Asp Thr Ile Gly Pro Leu Asp Ser Ser Ile Val Ser Leu Val Glu Glu
1               5                   10                  15

Thr Ser Phe Ile
            20
```

```
<210> SEQ ID NO 40
<211> LENGTH: 20
<212> TYPE: PRT
<213> ORGANISM: Human papilloma virus

<400> SEQUENCE: 40

Glu Pro Val Gly Pro Ser Glu Pro Ser Ile Val Gln Leu Val Glu Asp
1               5                   10                  15

Ser Ser Val Ile
            20

<210> SEQ ID NO 41
<211> LENGTH: 20
<212> TYPE: PRT
<213> ORGANISM: Human papilloma virus

<400> SEQUENCE: 41

Glu Pro Val Gly Pro Thr Asp Pro Ser Ile Val Thr Leu Val Glu Asp
1               5                   10                  15

Ser Ser Val Val
            20

<210> SEQ ID NO 42
<211> LENGTH: 20
<212> TYPE: PRT
<213> ORGANISM: Human papilloma virus

<400> SEQUENCE: 42

Asp Leu Trp His His Thr Glu Pro Ser Ile Val Asn Leu Val Glu Asp
1               5                   10                  15

Ser Ser Ile Ile
            20

<210> SEQ ID NO 43
<211> LENGTH: 20
<212> TYPE: PRT
<213> ORGANISM: Human papilloma virus

<400> SEQUENCE: 43

Glu Pro Ile Gly Pro Leu Glu Pro Ser Ile Val Ser Met Ile Glu Glu
1               5                   10                  15

Thr Thr Phe Ile
            20

<210> SEQ ID NO 44
<211> LENGTH: 20
<212> TYPE: PRT
<213> ORGANISM: Human papilloma virus

<400> SEQUENCE: 44

Glu Ser Val Gly Pro Thr Asp Pro Ser Ile Val Thr Leu Val Glu Glu
1               5                   10                  15

Ser Ser Val Ile
            20

<210> SEQ ID NO 45
<211> LENGTH: 20
<212> TYPE: PRT
<213> ORGANISM: Human papilloma virus
```

-continued

```
<400> SEQUENCE: 45

Glu Pro Val Gly Pro Thr Asp Pro Ser Ile Val Thr Leu Val Glu Asp
1               5                   10                  15

Ser Ser Val Ile
            20

<210> SEQ ID NO 46
<211> LENGTH: 20
<212> TYPE: PRT
<213> ORGANISM: Human papilloma virus

<400> SEQUENCE: 46

Glu Ser Val Gly Pro Thr Asp Pro Ser Ile Val Thr Leu Val Glu Glu
1               5                   10                  15

Ser Ser Val Ile
            20

<210> SEQ ID NO 47
<211> LENGTH: 20
<212> TYPE: PRT
<213> ORGANISM: Human papilloma virus

<400> SEQUENCE: 47

Glu Pro Val Gly Pro Thr Glu Pro Ser Ile Val Gln Leu Val Glu Asp
1               5                   10                  15

Ser Ser Val Ile
            20

<210> SEQ ID NO 48
<211> LENGTH: 20
<212> TYPE: PRT
<213> ORGANISM: Human papilloma virus

<400> SEQUENCE: 48

Thr Ser Val Gly Pro Ser Asp Ser Ser Ile Val Ser Leu Val Glu Glu
1               5                   10                  15

Ser Ser Phe Ile
            20
```

What is claimed is:

1. A capsid which is an aggregate formed by assembly of chimeric protein composed of human papillomavirus (HPV) 16 L1 protein and an HPV16 L2 epitope inserted in the loop region of the HPV16 L1 protein, wherein the region for insertion of the L2 epitope is a region of amino acids 430 to 433 and the L2 epitope has an amino acid sequence represented by: GGLGIGTGSGTGGRTGYIPL (SEQ ID NO: 3) (hereinafter, referred to as 56-75 L2 epitope).

2. The capsid according to claim 1, wherein the aggregate is an aggregate formed by assembly of multiple pentamer capsomeres, wherein each pentamer capsomere is composed of five chimeric protein molecules.

3. The capsid according to claim 2, wherein the aggregate formed by assembly of multiple pentamer capsomeres has a particle structure.

4. The capsid according to claim 3, wherein the number of the pentamer capsomeres constituting the aggregate is in the range of 65 to 80.

5. The capsid according to claim 3, wherein the number of the pentamer capsomeres constituting the aggregate is 72.

6. The capsid according to any one of claims 1 and 2 to 5, which is used for production of an L1 capsid immunogenic composition.

7. A chimeric protein composed of human papillomavirus (HPV) 16 L1 protein and an HPV16 L2 epitope inserted in the loop region of the HPV16 L1 protein, wherein the loop region for insertion of the L2 epitope is a region of amino acids 430 to 433, and the L2 epitope has an amino acid sequence represented by:

GGLGIGTGSGTGGRTGYIPL (SEQ ID NO: 3) (hereinafter, referred to as 56-75 L2 epitope).

8. A method of producing the capsid according to any one of claims 1 and 2 to 5, wherein the capsid is formed by assembly of the chimeric protein according to claim 7.

* * * * *